United States Patent [19]

Nakauchi et al.

[11] Patent Number: 5,045,228

[45] Date of Patent: Sep. 3, 1991

[54] OPTICALLY ACTIVE COMPOUND HAVING XI-VALEROLACTONE RING AND LIQUID CRYSTAL COMPOSITION COMPRISING SAME

[75] Inventors: Jun Nakauchi, Tokyo; Mioko Uematsu, Kawasaki; Keiichi Sakashita, Akishima; Yoshitaka Kageyama; Kenji Mori, both of Tokyo, all of Japan

[73] Assignee: Mitsubishi Rayon Company Ltd., Japan

[21] Appl. No.: 463,814

[22] Filed: Jan. 16, 1990

Related U.S. Application Data

[63] Continuation of Ser. No. 260,207, Oct. 20, 1988, abandoned.

[30] Foreign Application Priority Data

Oct. 23, 1987 [JP] Japan .................. 62-267712

[51] Int. Cl.$^5$ .............. C09K 19/34; C07D 309/30; C07D 239/02
[52] U.S. Cl. ................. 252/299.61; 252/299.65; 252/299.66; 252/299.67; 549/292; 549/293; 544/298; 544/335
[58] Field of Search ........ 252/299.61, 299.63, 252/299.66, 299.67, 299.65; 549/273, 292, 293; 544/298, 335

[56] References Cited

U.S. PATENT DOCUMENTS 4,818,431 4/1989 Eidenschink et al. ......... 252/299.61
4,909,957 3/1990 Sakaguchi ................ 252/299.61

Primary Examiner—John S. Maples
Assistant Examiner—Philip Tucker
Attorney, Agent, or Firm—Finnegan, Henderson, Farabow, Garrett & Dunner

[57] ABSTRACT

An optically active compound having a δ-valerolactone ring which is a ferroelectric liquid crystal and is represented by the following general formula (I):

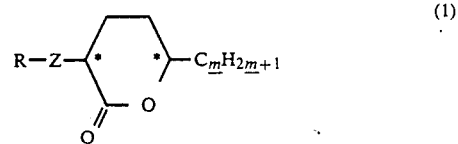

wherein m is an integer of from 1 to 8, Z is a group represented by the following formula:

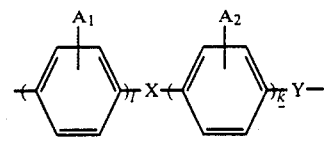

in which each of l and k is a number of 1 or 2 and l and k satisfy the requirement of $2 \leq (l+k) \leq 3$, X stands for a direct bond,

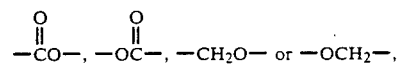

Y stands for

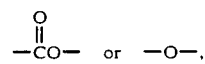

and
$A_1$ and $A_2$ independently stand for —H, —F or —Cl, (Abstract continued on next page.)

-continued
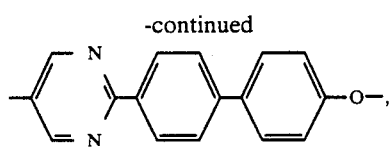
R stands for
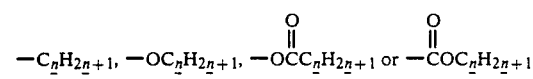
in which n is an integer of from 1 to 18, and * indicates the asymmetric carbon atom.
2 Claims, 6 Drawing Sheets

OPTICALLY ACTIVE COMPOUND HAVING XI-VALEROLACTONE RING AND LIQUID CRYSTAL COMPOSITION COMPRISING SAME

This application is a continuation of application Ser. No. 07/260,207, filed Oct. 20, 1988, now abandoned.

BACKGROUND OF THE INVENTION (1) Field of the Invention

The present invention relates to a novel δ-valerolactone ring-containing, optically active compound, which is valuable as a ferroelectric liquid crystal or an additive to a ferroelectric liquid crystal, and a liquid crystal composition comprising this optically active compound.

(2) Description of the Related Art

The mesophase of the liquid crystals currently widely used in a light-receiving type display belongs to the nematic phase, and therefore, the display is characterized in that it does not cause eye fatigue and consumes very little energy. However, this type of display has problems in that the response speed is low and the display cannot be seen from a certain angle.

A display device or printer head using a ferroelectric liquid crystal having a much higher response speed and contrast than those of a nematic liquid crystal has been investigated.

A ferroelectric liquid crystal was discovered for the first time by R. B. Meyer et al in 1975 [J. Physique, 36, L-69-71 (1975)]. This ferroelectric liquid crystal belongs to the chiral smectic C phase (hereinafter referred to as "Sm*C phase"), and a typical compound of this ferroelectric liquid crystal is p-decyloxybenzylidene-p'-amino-2-methylbutyl cinnamate (hereinafter referred to as "DOBAMBC") represented by the following formula (2):

$$C_{10}H_{21}O-\phantom{x}-CH=N-\phantom{x}=CH=CH-CO_2-CH_2-\overset{*}{C}HC_2H_5 \quad \overset{|}{CH_3} \quad (2)$$

In addition to DOBMBC, the ferroelectric liquid crystal materials prepared to date have a problem in that the temperature range showing the ferroelectric characteristics (the temperature range wherein the Sm*C phase is present) is narrow, and therefore, attempts have been made to expand the temperature range showing the Sm*C phase to the lower and higher temperature sides, taking room temperature as the center, by mixing several ferroelectric liquid crystals. Accordingly, the development of a ferroelectric liquid crystal having the Sm*C phase present in a practical temperature range is desired, and further, a ferroelectric crystal having a larger spontaneous polarization than that of the known ferroelectric liquid crystals is desired as a liquid crystal for a printer head for which an ultra-high response speed is required.

SUMMARY OF THE INVENTION

Therefore, a primary object of the present invention is to provide a novel compound which is chemically stable, does not undergo undesirable coloration, has an excellent photostability, exhibits an enhanced spontaneous polarization, and is valuable as a ferroelectric liquid crystal or an additive to a ferroelectric liquid crystal.

In one aspect of the present invention, there is provided an optically active compound having a δ-valerolactone ring, which is represented by the following general formula (1) and a liquid crystal composition comprising this optically active compound:

$$R-Z-\underset{O}{\overset{*}{\diagdown}}\underset{O}{\overset{*}{\diagup}}-C_mH_{2m+1} \quad (1)$$

wherein m is an integer of from 1 to 8, Z is a group represented by the following formula $$-\underset{}{\overset{A_1}{\diagdown}}{}_l-X-\underset{}{\overset{A_2}{\diagdown}}{}_k-Y-$$

in which each of l and k is a number of 1 or 2 and l and k satisfy the requirement of $2 \leq (l+k) \leq 3$, X stands for a direct bond, $$-\overset{O}{\overset{\|}{C}}O-, -O\overset{O}{\overset{\|}{C}}-, -CH_2O- \text{ or } -OCH_2-,$$

Y stands for $$-\overset{O}{\overset{\|}{C}}O- \text{ or } -O-,$$

and $A_1$ and $A_2$ independently stand for —H, —F, or —Cl,

[three heterocyclic N-containing ring structures shown with —O— substituents]

R stands for $$-C_nH_{2n+1}, -OC_nH_{2n+1}, -O\overset{O}{\overset{\|}{C}}C_nH_{2n+1} \text{ or } -\overset{O}{\overset{\|}{C}}OC_nH_{2n+1}$$

in which n is an integer of from 1 to 18, and * indicates the asymmetric carbon atom.

In another aspect of the present invention, there is provided a liquid crystal composition comprising the above-mentioned optically active compound.

DESCRIPTION OF THE PREFERRED EMBODIMENTS

Figure 1:
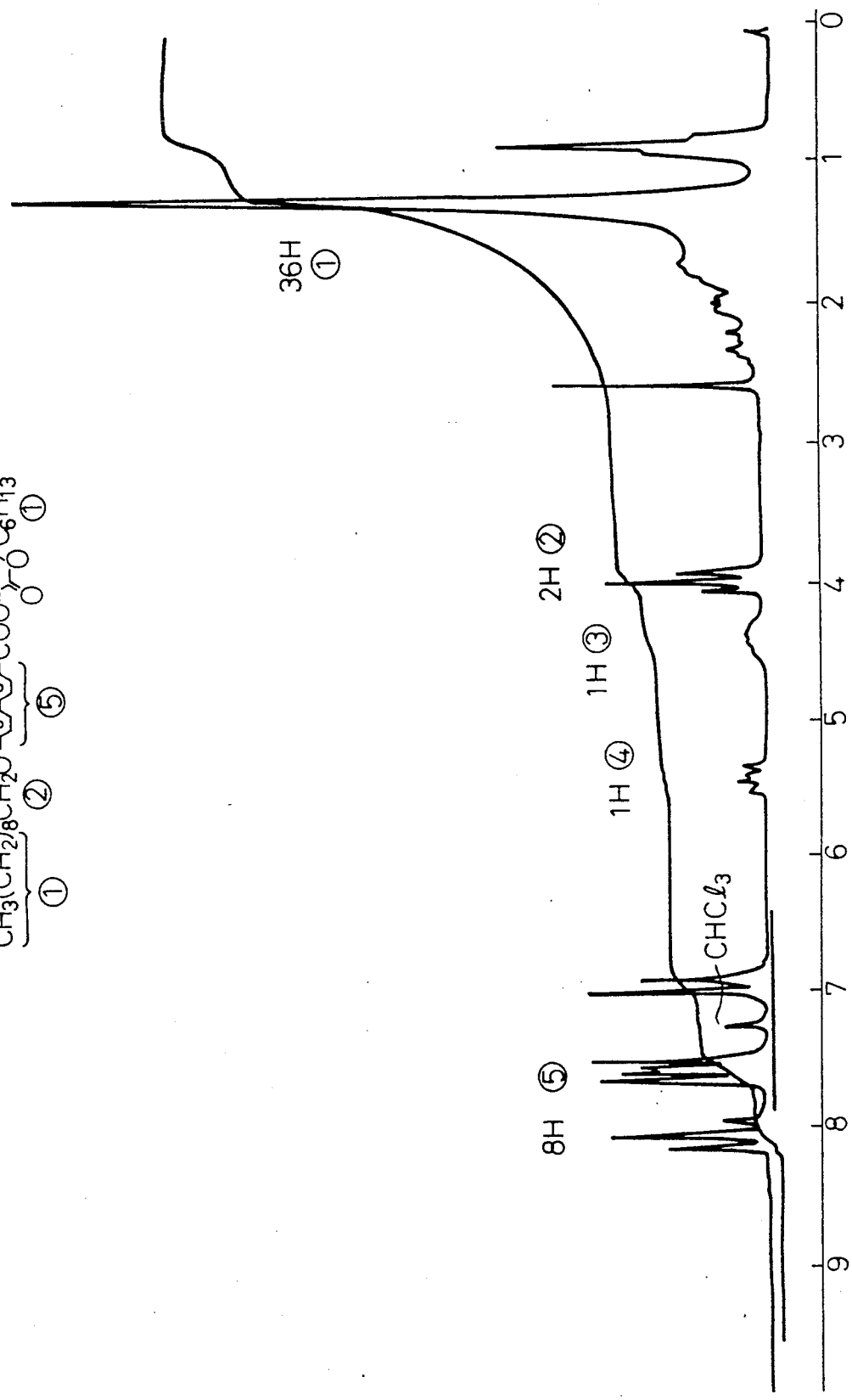
FIGS. 1 and 2 illustrate NMR spectra of examples of the optically active compound of the present invention.

If the carbon number (n) of the alkyl group $C_nH_{2n+1}$ in R in the formula (1) is 19 or larger, it is rather difficult to purify the following compounds:

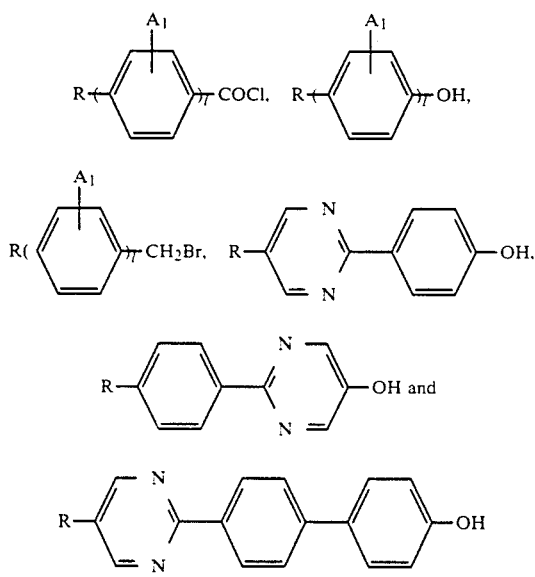

where in l is 1 or 2, which are used as intermediate substances. If the carbon number (m) of the alkyl group $C_mH_{2m+1}$ in the formula (1) is 9 or larger, it is difficult to purify the optically active lactone. In each case, the productivity is reduced, and when the optically active lactone is mixed with other liquid crystals, a tendency toward a reduction of the spontaneous polarization is undesirably observed.

The process for the synthesis of the optically active compound of the present invention will now be described.

The starting compound used in this synthesis process, which is represented by the following formula:

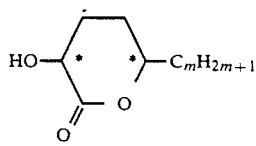

wherein m is an integer of from 1 to 8, is obtained by subjecting an optically active β-acetoxycarboxylic acid and a monoester of an optically active α-acetoxydibasic acid to electrode reaction by the Kolbe electrolysis process and cyclizing the reaction product.

More specifically, a methyl alkyl ketone is reacted with diethyl carbonate in the presence of sodium hydride to form an ethyl ester of a β-ketocarboxylic acid, as expressed by the following formula:

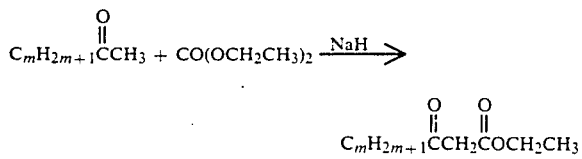

This ethyl ester is hydrolyzed with potassium hydroxide, as expressed by the following formula:

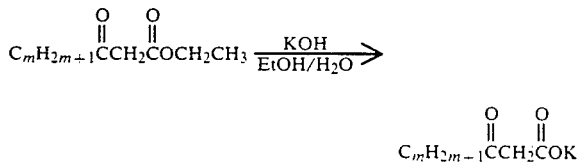

Then, the carbonyl group at the β-position is asymmetrically reduced by using baker's yeast to form an optically active β-hydroxycarboxylic acid, as expressed by the following formula:

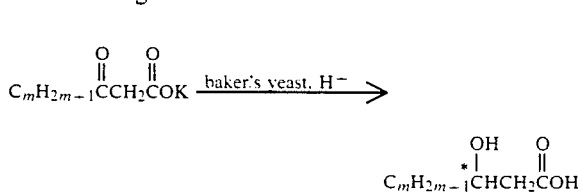

This carboxylic acid is reacted with acetic anhydride in pyridine to obtain a β-acetoxycarboxylic acid, as expressed by the following formula:

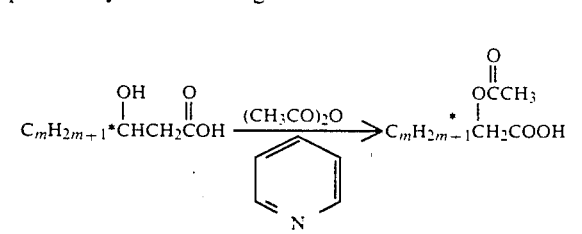

Separately, S—(—)—malic acid is reacted with acetyl chloride, and the obtained reaction product is reacted with absolute ethanol to obtain a monoethyl ester of an optically active α-acetoxy-dibasic acid, as expressed by the following formula [Tetrahedron Letters, 41 No. 13, 2751–2758 (1985)]:

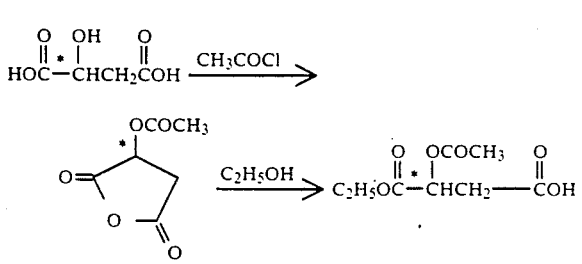

The thus-obtained optically active β-acetoxycarboxylic acid and the thus-obtained monoethyl ester of the optically active α-acetoxy-dibasic acid are subjected to electrode reaction by the Kolbe electrolysis process, as expressed by the following formula:

$$C_mH_{2m+1}\overset{*}{\underset{OCOCH_3}{C}}HCH_2COOH + C_2H_5O\overset{O}{C}-\overset{*}{\underset{OCOCH_3}{C}}HCH_2-\overset{O}{C}OH \longrightarrow$$

$$C_mH_{2m+1}\overset{*}{\underset{OH}{C}}HCH_2CH_2\overset{*}{C}H\overset{O}{C}OH$$
$$\underset{OH}{|}$$

The obtained product is cyclized in the presence of p-toluenesulfonic acid to obtain the above-mentioned valerolactone derivative, as expressed by the following formula:

$$C_mH_{2m+1}-\overset{*}{\underset{OH}{C}}HCH_2CH_2\overset{*}{C}H\overset{O}{C}OH \longrightarrow$$

[structure: $C_mH_{2m+1}$—valerolactone with OH]

[Synthesis of Compound Represented by General Formula (1)]

The compound represented by the general formula (1) can be synthesized according to the following routes.

(a) Compound where Y in Z in general formula (1) is $$-\overset{O}{\underset{\|}{C}}O-$$

(a-1) where X × direct bond

[structure: R—(A₁ ring)—(A₂ ring)—COCl +]

[structure: HO-valerolactone-$C_mH_{2m+1}$] $\xrightarrow{Et_2N}$

[structure: R—(A₁)—(A₂)—CO—valerolactone—$C_mH_{2m+1}$]

(R, m, A₁ and A₂ are as defined above.)
(a-2) where $$X = -\overset{O}{\underset{\|}{C}}O-$$

[structure: CH₃CO—(A₂ ring)ₖ—COCl +]

[structure: HO-valerolactone-$C_mH_{2m+1}$] $\xrightarrow{Et_3N}$

[structure: CH₃CO—(A₂)ₖ—CO—valerolactone—$C_mH_{2m+1}$]

$\xrightarrow[\text{MeOH/THF}]{\text{Equimolar 1N LiOH}}$

[structure: HO—(A₂)ₖ—CO—valerolactone—$C_mH_{2m+1}$]

[structure: HO—(A₂)ₖ—CO—valerolactone—$C_mH_{2m+1}$ +]

[structure: R—(A₁)ₗ—COCl] $\xrightarrow{Et_3N}$

[structure: R—(A₁)ₗ—CO—(A₂)ₖ—CO—valerolactone—$C_mH_{2m+1}$]

(R, m, l, k, A₁ and A₂ are as defined above.)
(a-3) Where X=—OCH₂—
  i) Where R=$C_nH_{2n+1}$O—

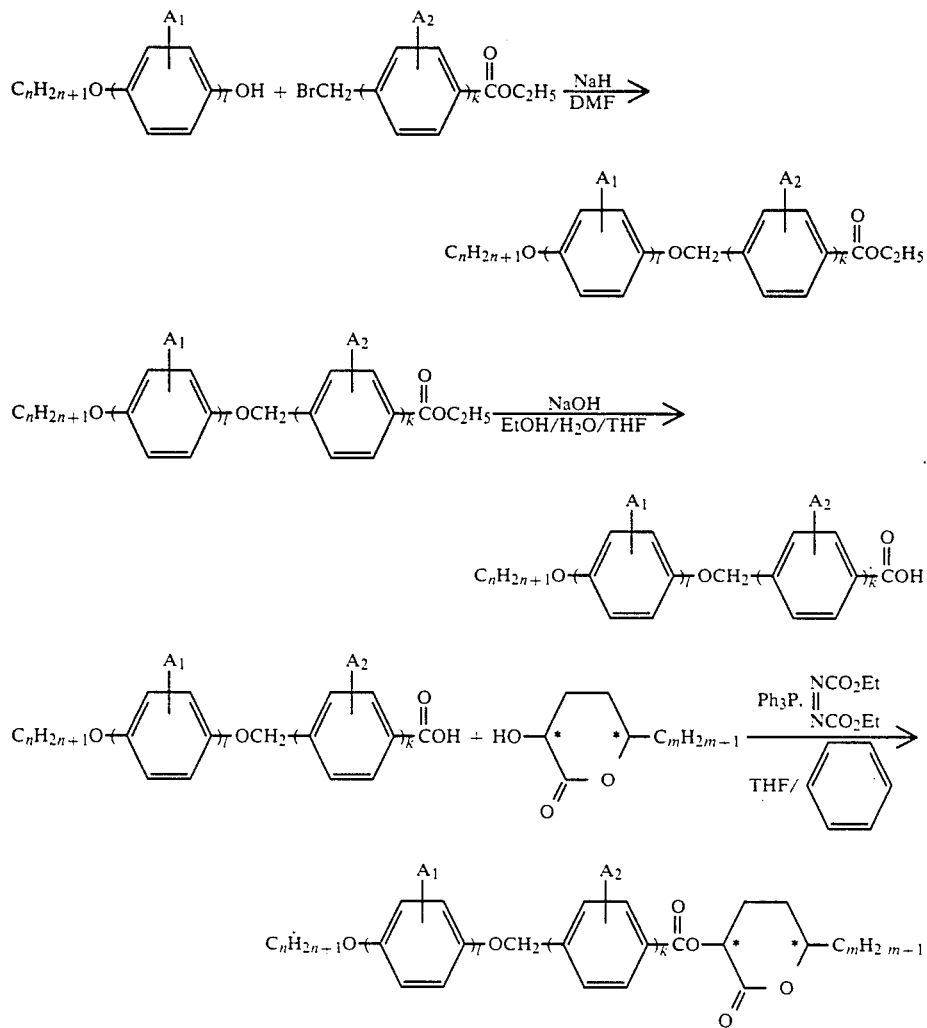
(n, l, k, m, $A_1$ and $A_2$ are as defined above.)
ii) Where
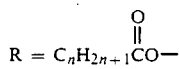
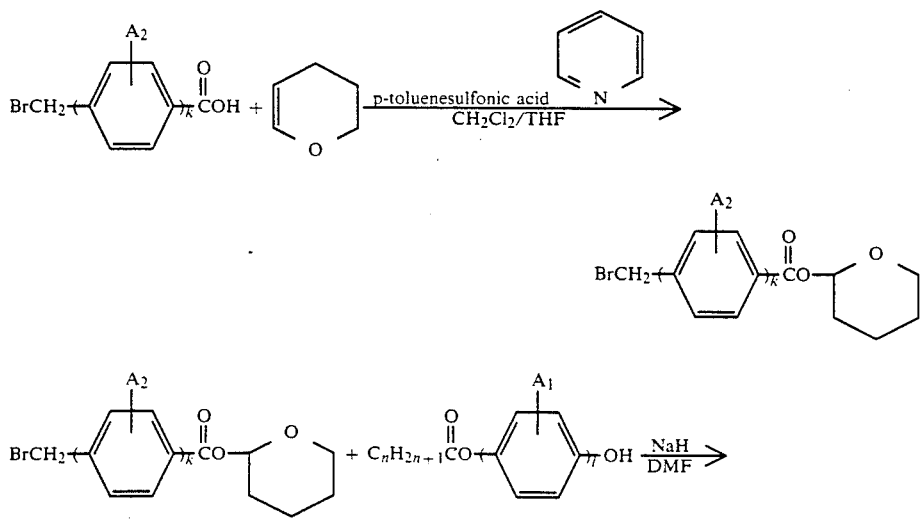

-continued
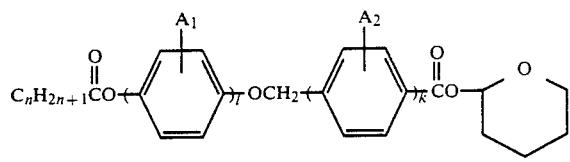
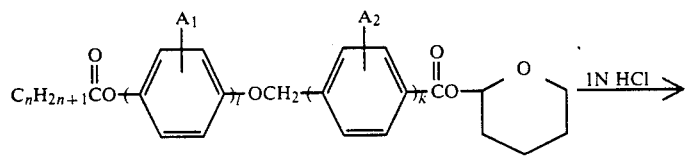
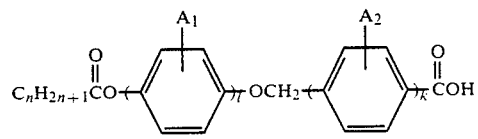
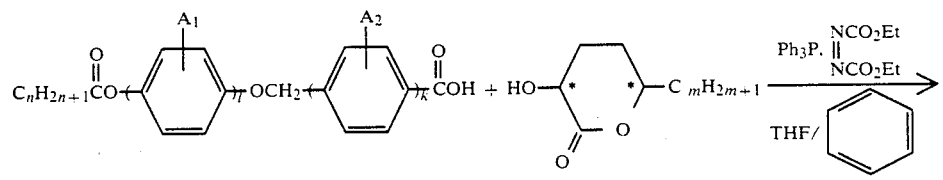
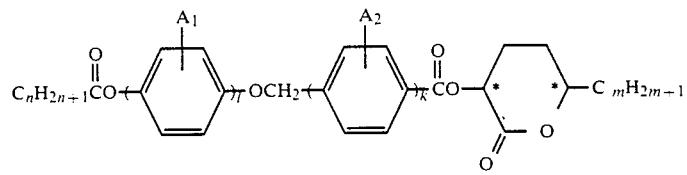
(n, m, l, k, $A_1$ and $A_2$ are as defined above.)
(a-4) Where $X=-CH_2O-$
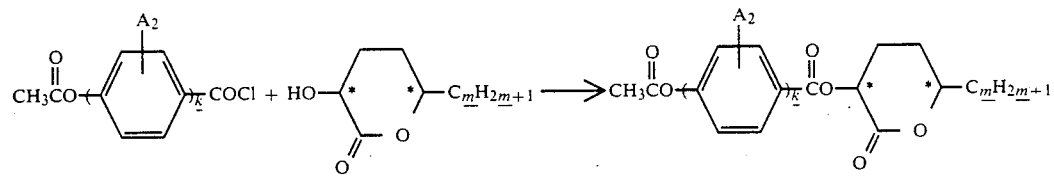
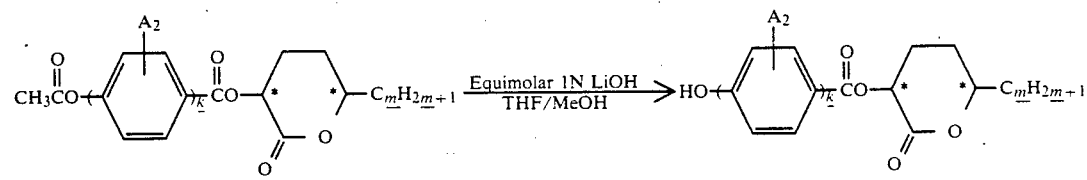
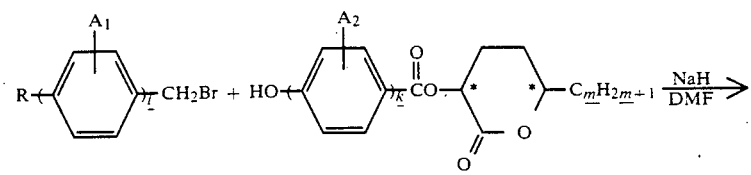

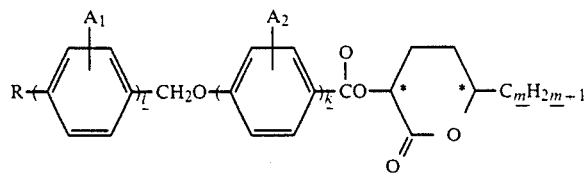
(R, l, k, m, $A_1$ and $A_2$ are as defined above.)
(a-5) Where
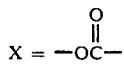
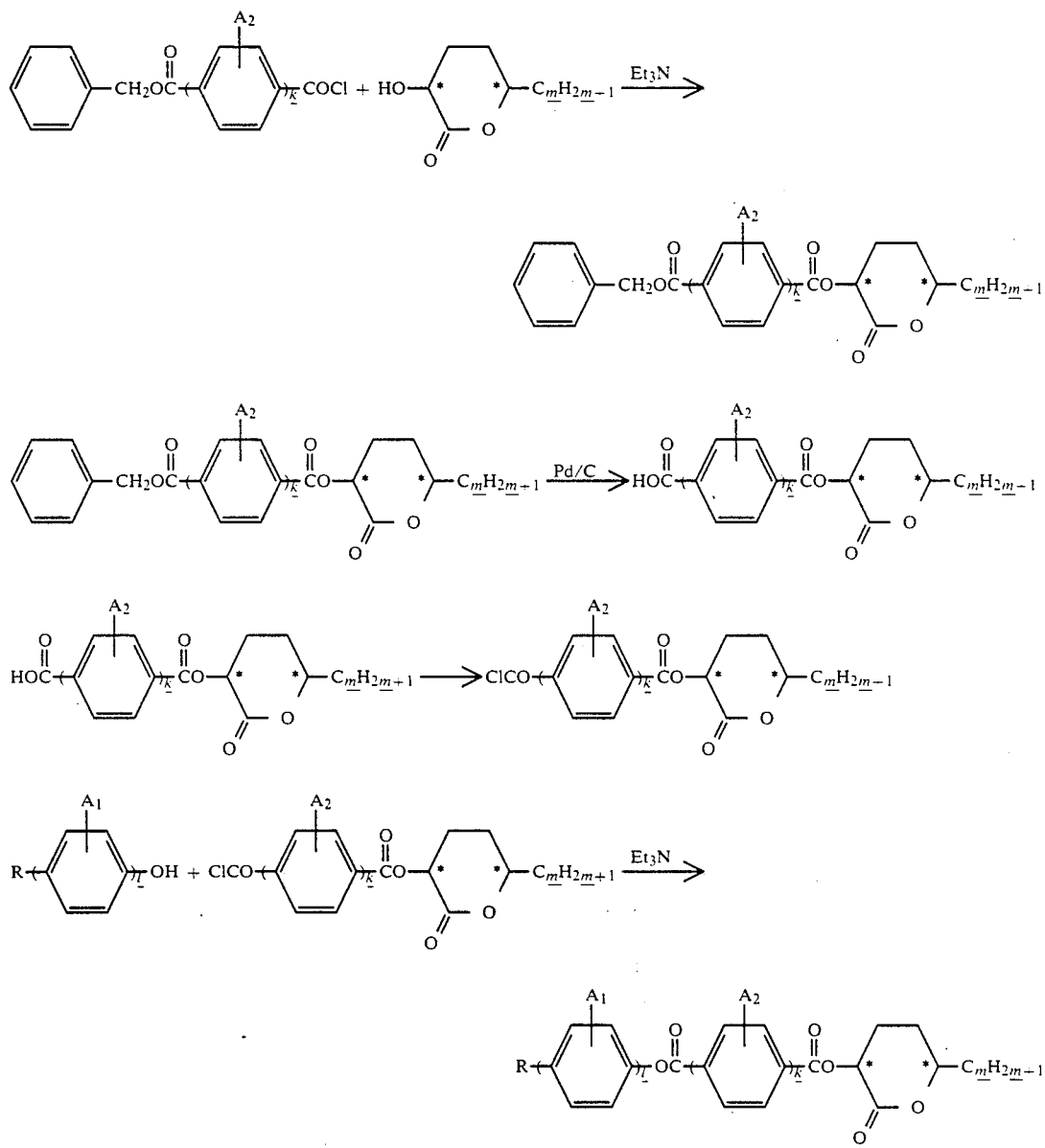
(R, l, k, m, $A_1$ and $A_2$ are as defined above.)
(b) Compound where Y in Z in general formula (1) is —O—
(b-1) Where X=direct bond
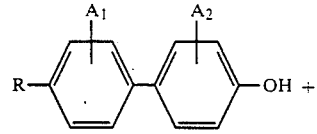

13
-continued
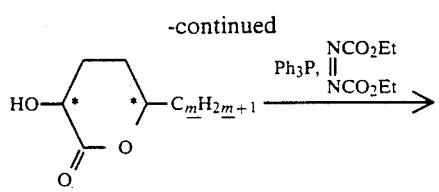
14
-continued
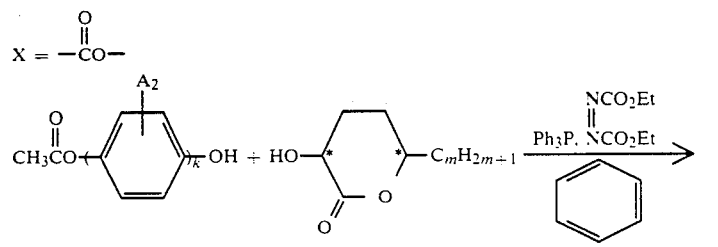
(R, m, $A_1$ and $A_2$ are as defined above.)
(b-2) Where
$$X = -\overset{O}{\underset{\|}{C}}O-$$
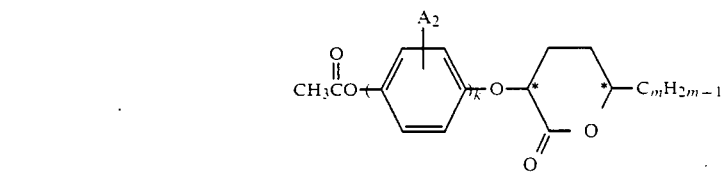
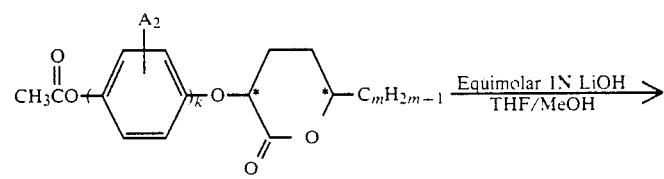
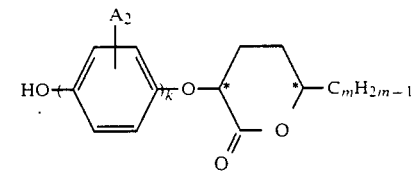
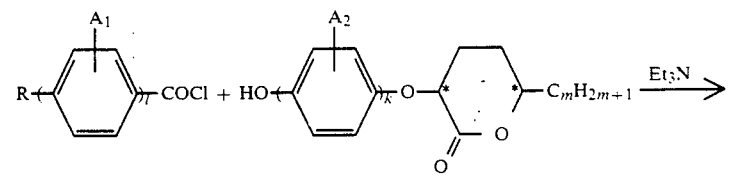
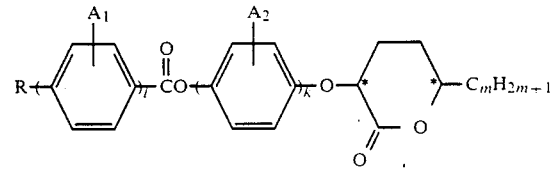
(R, k, l, m, $A_1$ and $A_2$ are as defined above.)
(b-3) Where $X = -OCH_2-$

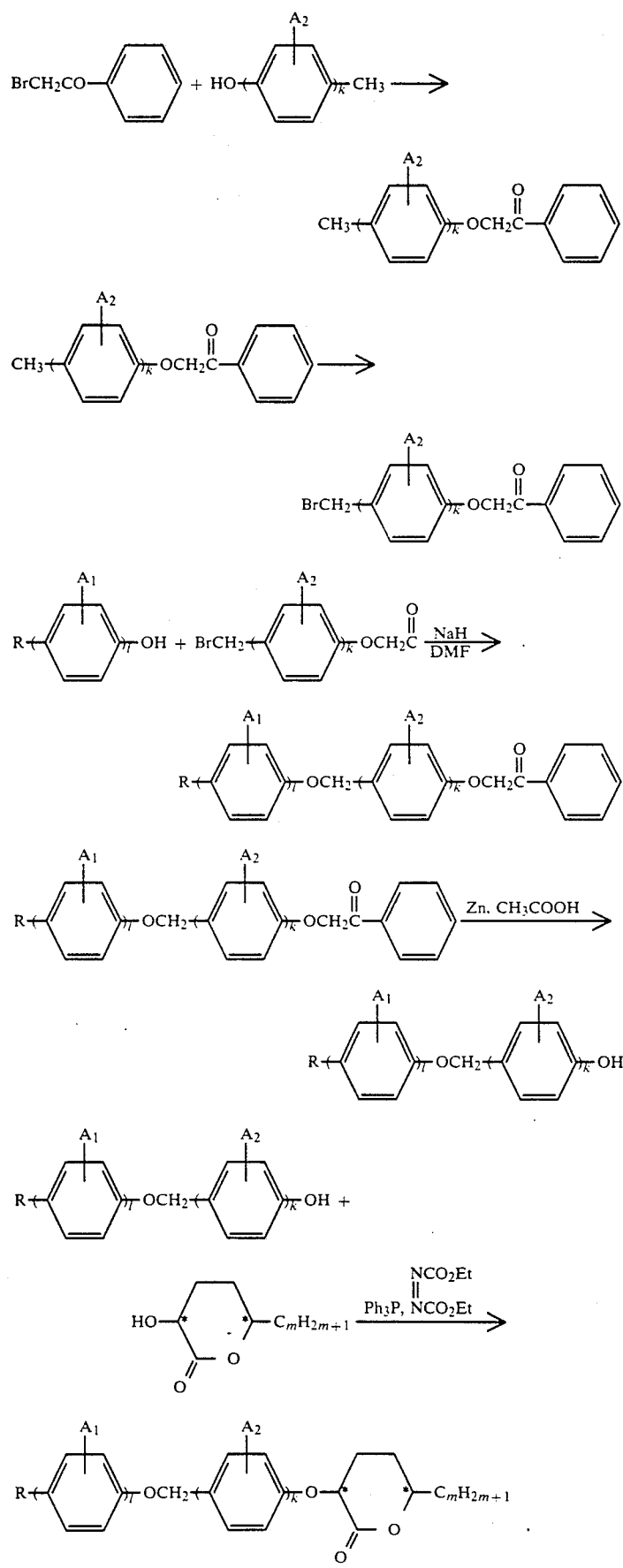

(R, l, k, m, $A_1$ and $A_2$ are as defined above.)
(a-4) Where X=—$CH_2O$—
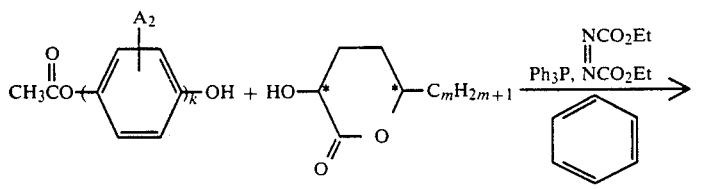
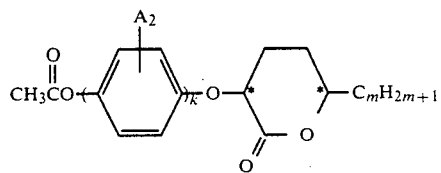
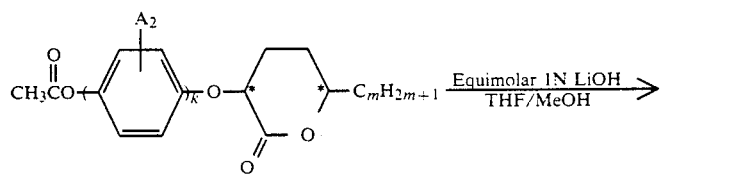
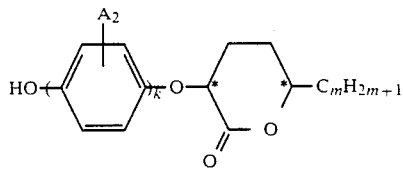
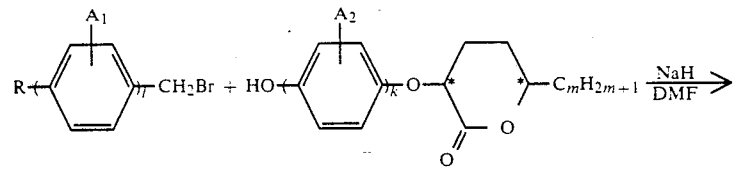
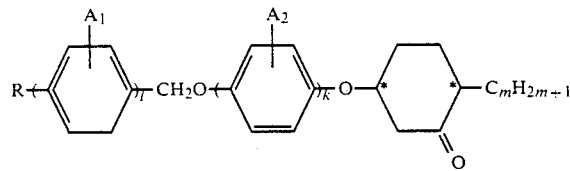
(R, l, k, m, $A_1$ and $A_2$ are as defined above.)
(a-5) Where
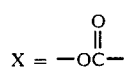
$$X = -O\overset{O}{\overset{\|}{C}}-$$
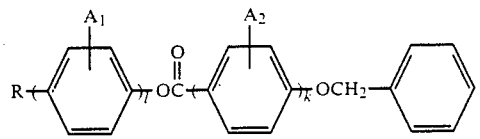
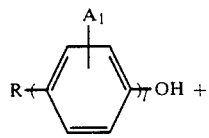
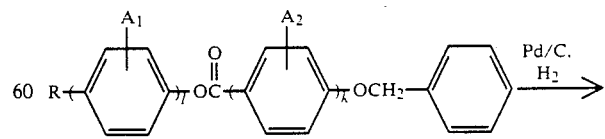
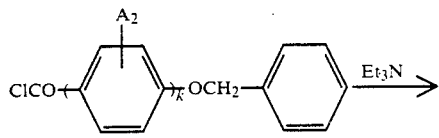
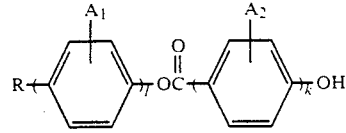

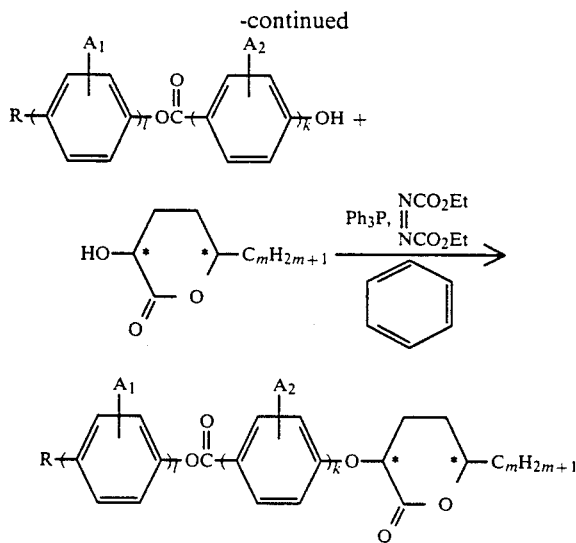

(R, l, k, m, $A_1$ and $A_2$ are as defined above.)

(c) Compound where Z in general formula (1) is

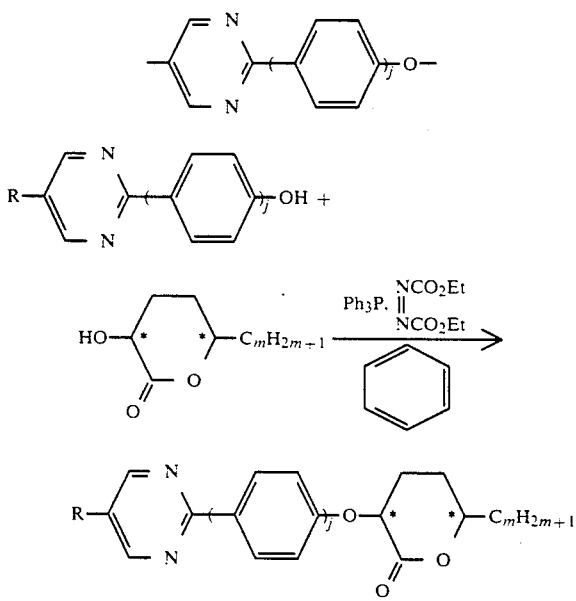

(j is 1 or 2, and R and m are as defined above.)

(d) Compound where Z in general formula (1) is

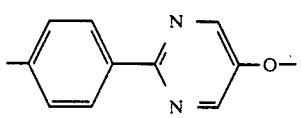

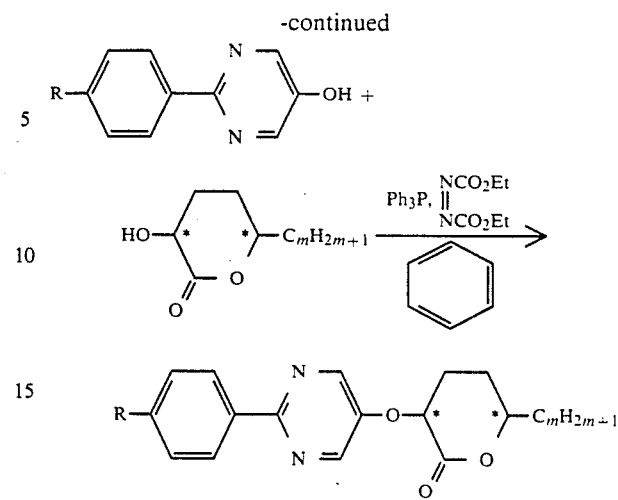

(R and M are as defined above.)

Since the compound of the present invention does not contain an azomethine bond inherently possessed by the conventional ferroelectric liquid crystal compounds, the chemical stability characteristics such as hydrolysis resistance are improved, discoloration does not occur and the light stability is improved as compared with cinnamic acid type compounds having a vinyl group. Therefore, the compound of the present invention possesses excellent characteristics required for a display material.

Most of the compounds included within the scope of the present invention shown the Sm*C phase in the practical temperature range and exhibits a very large spontaneous polarization of scores to several hundreds of $nC/cm^2$, and therefore, they are practically valuable.

Of the compounds included within the scope of the present invention, those not showing the Sm*C phase are characterized in that when they are mixed with other liquid crystal materials showing the SmC phase or ferroelectric liquid crystal materials, the Sm*C phase-showing temperature range is expanded and the spontaneous polarization is increased.

The liquid crystal composition of the present invention will now be described.

The liquid crystal composition of the present invention comprises at least one compound represented by the general formula (1). A liquid crystal composition comprising a plurality of ferroelectric liquid crystal compounds, optionally with another additive compound, is superior to a liquid crystal composition comprising one liquid crystal compound alone because the applicable temperature range is broadened.

As specific examples of other ferroelectric liquid crystals that can be mixed with at least one compound represented by the general formula (1), there can be mentioned compounds having the following molecular structures:

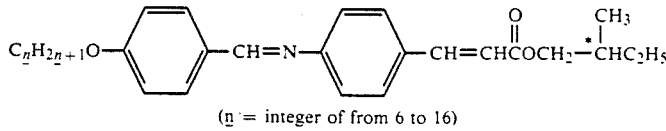

(n = integer of from 6 to 16)

-continued
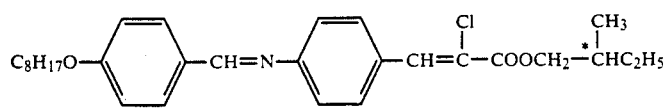
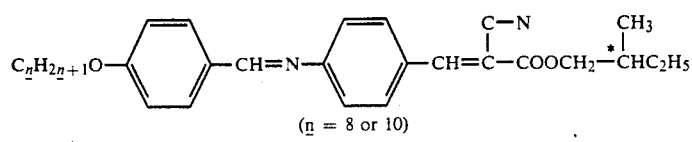
(n = 8 or 10)
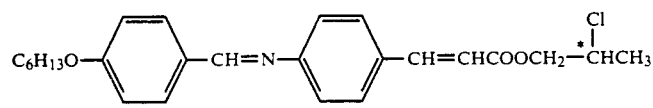
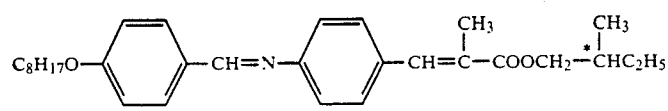
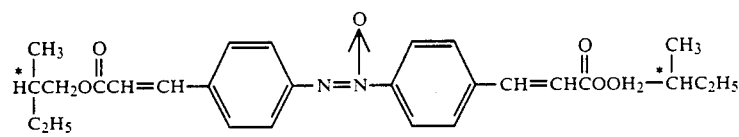
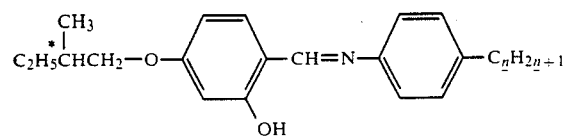
(n = integer of from 7 to 10)
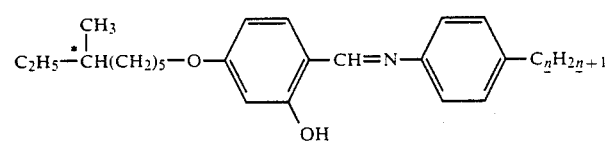
(n = integer of from 7 to 14)
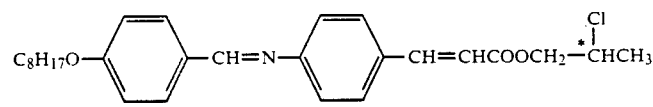
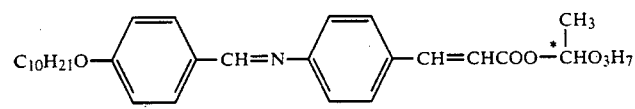
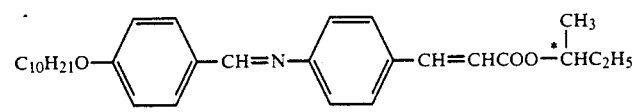
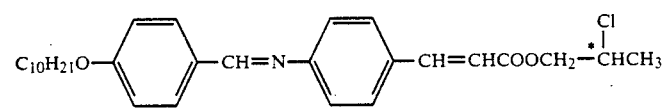
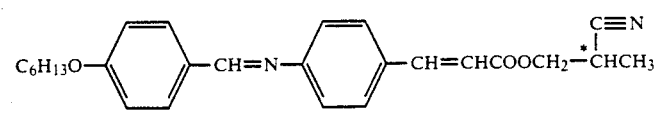

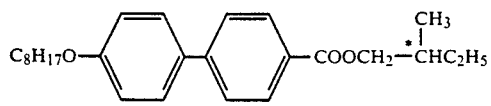

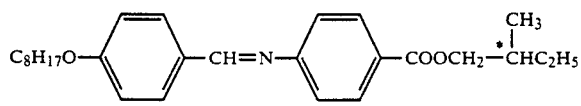

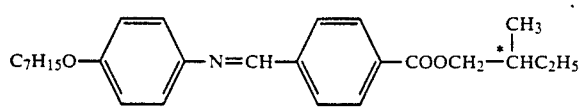

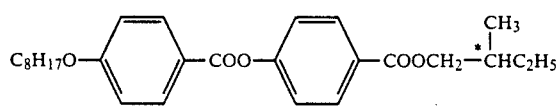

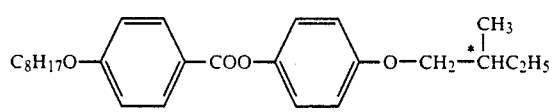

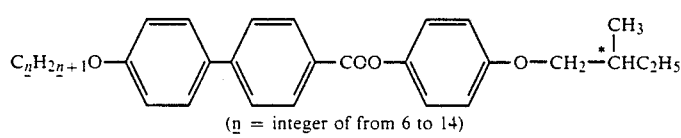

(n = integer of from 6 to 14)

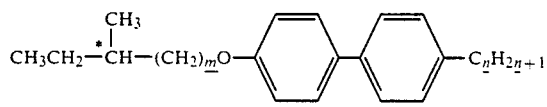

(m = integer of from 2 to 5,
n = integer of from 8 to 12)

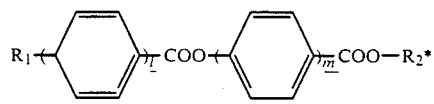

[l, m = 1 or 2, R₁ = $C_nH_{2n+1}O-$ or $C_nH_{2n+1}-$ (n = 8 to 10),

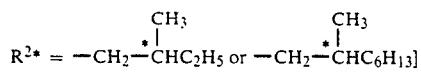

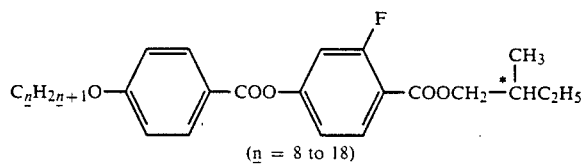

(n = 8 to 18)

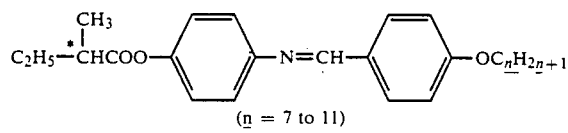

(n = 7 to 11)

Other liquid crystal compounds having no ferroelectric characteristics can be mixed with the compound represented by the formula (1), as long as they show the Sm*C phase. Furthermore, mixtures of two or more of the foregoing compounds can be mixed with the compound represented by the formula (1).

The present invention will now be described in detail with reference to the following examples.

REFERENTIAL EXAMPLE 1

Synthesis of β-acetoxynonanoic acid

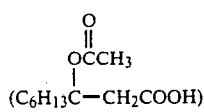

A solution of 20.0 g of methyl hexyl ketone in 100 ml of dioxane was dropped into a solution comprising 210 ml of diethyl carbonate, 12.8 g of sodium hydride dispersed in oil at a concentration of 60% by weight and 100 ml of dioxane in an argon atmosphere, and the mixture was refluxed overnight. Then, the solvent was removed and the residue was distilled under a reduced pressure to obtain 20.0 g of ethyl hexylketoacetate having a boiling point of 83° C. under 0.65 mmHg. The yield was 62.5%.

In a solution comprising 75 ml of ethanol, 75 ml of distilled water and 5.02 g of potassium hydroxide was dissolved 15 g of ethyl hexylketoacetate, and the solution was stirred at room temperature for 7.5 hours to the solution were added 3 l of distilled water, 360 g of sucrose and 168 g of dry yeast. The mixture was shaken at 30° C. for 16 hours and filtered with Celite ™. The precipitate was air-dried and extracted with ethyl acetate, and the extract was concentrated. Separately, hydrochloric acid was added to the filtrate to adjust the pH value to 1, and sodium chloride was added to form a saturated solution. The solution was extracted with chloroform and the extract was concentrated. The thus-formed concentrate and the above-mentioned concentrate were dissolved together in diethyl ether, and the solution was extracted twice with a 1N aqueous solution of sodium hydroxide. Hydrochloric acid and sodium chloride were added to the extract again to form a saturated aqueous solution of sodium chloride having a pH value of 1. The solution was extracted 5 times with ether, and the ether layer was washed with a saturated aqueous sodium chloride solution and dehydrated on magnesium sulfate. The ether was then evaporated and the residue was recrystallized from n-hexane to obtain 7.81 g of β-hydroxynonanoic acid having a melting point of 49.3 to 50.0° C. and $[\alpha]^{24.5}$ of $-20.1°$.

Then 5.0 g of this β-hydroxynonanoic acid was mixed with 20 ml of anhydrous pyridine and 3.2 ml of acetic anhydride under ice cooling, and the mixture was stirred at room temperature overnight and cooled with ice. Then, 5 ml of distilled water was added to the mixture, the mixture was dissolved in 1N hydrochloric acid, and the solution was extracted with ether. The ether layer was washed with a saturated aqueous sodium chloride solution and dehydrated on magnesium sulfate. Then, the ether was evaporated and the residue was concentrated to obtain 5.4 g of β-acetoxynonanoic acid.

REFERENTIAL EXAMPLE 2

Synthesis of β-acetoxybutanoic acid

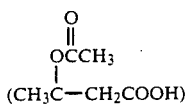

In a mixture of 36 ml of absolute ethanol and 36 ml of anhydrous 1,2-dichloroethane was suspended 5 g of optically active poly-β-hydroxybutylate and 1.1 ml of concentrated sulfuric acid was added to the suspension. The mixture was heated and refluxed for 57 hours and then cooled, and 15 ml of a saturated aqueous sodium chloride solution was added. Celite ™ was suspended in the mixture and the mixture was filtered. The filtrate was extracted once with 70 ml of ether and three times with 20 ml of ether, and the residue was washed with 100 ml of ether. The ether washing was combined with the extract. The mixture was washed with a saturated aqueous sodium hydrogencarbonate solution and with a saturated aqueous sodium chloride solution and dried on magnesium sulfate. Then, the ether was removed and the residue was distilled under a reduced pressure to obtain 4.0 g of ethyl (R)-β-hydroxybutanoate having $[\alpha]^{21.5}$ of $+43.9°$.

In a liquid mixture comprising 15 ml of water, 15 ml of ethanol and sodium hydroxide was dissolved 4.0 of ethyl (R)-β-hydroxybutanoate, and the solution was refluxed under heating, cooled and passed through an ion exchange resin (Amberlite½ IR-120B). The solvent was removed under a reduced pressure, 10 ml of anhydrous pyridine and 3 ml of anhydrous acetic acid were added to the residue, and the mixture was stirred at room temperature overnight. Dilute hydrochloric acid was added to the reaction liquid to adjust the pH value to 1, and the reaction liquid was saturated with sodium chloride and extracted with chloroform. The extract was washed with a saturated aqueous sodium chloride solution and dehydrated on magnesium sulfate. Then, chloroform was removed under a reduced pressure to obtain 3.6 g of the intended compound having $[\alpha]^{24}$ of $-5.7°$.

REFERENTIAL EXAMPLE 3

Synthesis of 1-ethyl S-(2)-acetoxybutanedioate

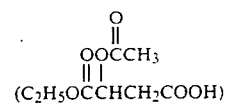

To 50 g of (S)—(—)—malic acid was added 160 ml of acetyl chloride, the mixture was refluxed at 55° C. with stirring for 4 hours, and the formed solution was concentrated under vacuum. Then, 100 ml of benzene was added to the residue, and benzene and acetic acid were removed under vacuum. The residue was concentrated and cooled to room temperature, and then 100 ml of absolute ethanol was added to the residue, and the mixture was violently stirred while cooling the mixture occasionally. The mixture was heated at 70° to 75° C. for 10 minutes and at 50° to 55° C. for 10 hours, the solvent was removed under a reduced pressure, and the residue was separated and purified in a silica gel column by using methylene chloride/methanol (50/1) as the developing solvent, to obtain 50.9 g of 1-ethyl S-(2)-acetoxybutanedioate having a melting point of 50 to 51° C. and $[\alpha]^{23}$ of $-31.6°$ C. (c=1.42, ethanol).

REFERENTIAL EXAMPLE 4

Synthesis of (2S,5R)-2-hydroxy-5-hexyl-δ-valerolactone

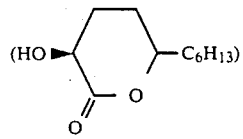

In methanol were dissolved 1.89 g of (R)-β-acetoxynonanoic acid synthesized in Referential Example 1 and 7.14 g of 1-ethyl S-(2)-acetoxybutanedioate, and Kolbe electrolysis was carried out for 7 hours under conditions of 20° to 30° C., 30 V and 1.5 A by a constant voltage electrolysis apparatus (Yanaco VE-8). After completion of the electrolysis, 40 ml of a 3N aqueous sodium hydroxide solution was added to the solution, and the mixture was stirred overnight. Methanol was removed and the residue was washed with ether. Hydrochloric acid was added to the separated alkali aqueous solution layer to adjust the pH value to 1, and sodium chloride was added to form a saturated aqueous solution. Then, the solution was extracted with chloroform, the extract was dehydrated on magnesium sulfate, and chloroform was evaporated to obtain 1.5 g of crude 3,6-dihydroxyundecylcarboxylic acid. This product was dissolved in 10 ml of benzene and a catalytic amount of p-toluenesulfonic acid was added, and the solution was stirred at room temperature for 2 hours and then dissolved in ether. The solution was washed three times with a saturated aqueous sodium bicarbonate solution and once with saturated aqueous sodium chloride solution and dried on magnesium sulfate. Ether was evaporated and the residue was concentrated. The concentrate was separated and purified in a silica gel column by using a liquid mixture of hexane and ethyl acetate as the developing solvent, and was recrystallized from a mixed solvent of n-hexane and ethyl acetate to obtain 245.1 mg of (2S,5R)-2-hydroxy-5-hexyl-δ-valerolactone.

Melting Point: 75.5° to 77.0° C.

| | Elementary Analysis Values: | | |
|---|---|---|---|
| | C(%) | H(%) | N(%) |
| Found values | 65.84 | 10.29 | 0.06 |
| Calculated values | 65.97 | 10.07 | 0 |
| Specific rotary power: | $[\alpha]_D^{25}$ = + 76.8° (c = 1.1 in chloroform) | | |
| $^1$H-NMR: | (δ ppm) 4.36 (2H), 3.21 (1H), 1.31 (14H), 0.89 (3H) | | |

(2S,5R)-2-hydroxy-5-methyl-δ-valerolactone was synthesized in the same manner as described above, except that (R)-β-acetoxynonanoic acid was used instead of (R)-β-acetoxynonanoic acid.

REFERENTIAL EXAMPLE 5

Synthesis of 4'-decyloxybiphenyl-4-carboxylic acid chloride

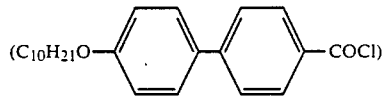

To 30 ml of methyl isobutyl ketone were added 3 g of 4-hydroxy-4'-cyanobiphenyl, 21.4 g of 1-bromodecane and 2.5 g of potassium carbonate, and the mixture was reacted under reflux for 30 hours. The reaction mixture was cooled and insoluble substances were removed by filtration. The filtrate was concentrated under a reduced pressure, ethanol was added to the residue and recrystallization was carried out to obtain 5 g of 4-decyloxy-4'-cyanobiphenyl. Thus, 4.1 g of this 4-decyloxy-4'-cyanobiphenyl was dissolved in 25 ml of ethylene glycol, 2.5 ml of 2N sodium hydroxide was added to the solution, and a reaction was carried out under reflux for 4 hours. The reaction liquid was put into dilute hydrochloric acid cooled by ice, and the precipitate was recovered by filtration, washed with water and ethanol, and dried. The dried product was recrystallized from chloroform to obtain 3.0 g of 4'-decyloxybiphenyl-4-carboxylic acid. Then, 20 g of thionyl chloride was dropped into this carboxylic acid and the mixture was reacted under reflux for 2 hours. Unreacted thionyl chloride was removed by distillation under a reduced pressure and 4'-decyloxybiphenyl-4-carboxylic acid chloride was quantitatively recovered.

In the same manner as described above, 4'-alkoxybiphenyl-4-carboxylic acid chlorides having different alkoxy chain lengths were synthesized.

REFERENTIAL EXAMPLE 6

Synthesis of 4-hydroxy-4'-decyloxybiphenyl

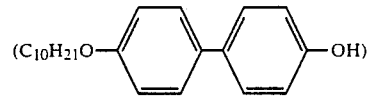

In 25 ml of methanol was dissolved 5.0 g of biphenyl, and a solution comprising 1.3 g of sodium hydroxide, 1 ml of water and 5 ml of methanol was added to the above solution. The mixture was refluxed under heating, a solution of 5.4 g of n-bromodecane in 5 ml of methanol was dropped into the formed solution, and the mixture was refluxed overnight. The reaction liquid was concentrated under a reduced pressure and the pH value was adjusted to 2 to 3 by water and hydrochloric acid. The mixture was extracted three times with chloroform, and the extract layer was washed with a saturated aqueous sodium chloride solution dried on magnesium sulfate, concentrated under a reduced pressure and purified by 4-hydroxy-4'-decyloxybiphenyl.

REFERENTIAL EXAMPLE 7

Synthesis of p-dodecyloxyphenyl-p'-carboxybenzyl ether

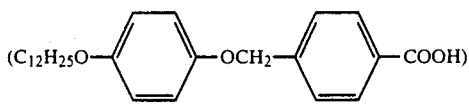

To 287 mg of sodium hydride washed with n-pentane was added 5 ml of dimethylformamide (DMF), and a solution of 20 g p-dodecyloxyphenol in 5 ml of DMF was dropped into the above mixture with stirring in a nitrogen atmosphere. The mixture was stirred for 1 hour and a solution of 2 g of ethyl p-bromomethylbenzoate in 5 ml of DMF was added to the mixture. Reaction was carried out for 3 hours with stirring, and the reaction mixture was put into a 1N aqueous hydrochloric acid solution and extracted with chloroform. The extract was concentrated and the precipitated crystal was washed with n-hexane and dried. The crystal was dissolved in a liquid mixture comprising ethanol, tetrahydrofuran and water and 5 ml of 1N NaOH was added to the solution. The mixture was heated at 60° C. and reacted for 1 hour, and the reaction mixture was cooled, and the precipitated crystal was recovered by filtration and dissolved in tetrahydrofuran. Then, a 1N aqueous hydrochloric acid solution was added to the above solution to precipitate a crystal again. The crystal was recovered by filtration and washed with water and ethanol to obtain 1.1 g of p-dodecyloxyphenyl-p'-carboxybenzyl ether.

Analogues having different alkyl chain lengths were similarly synthesized.

REFERENTIAL EXAMPLE 8

Synthesis of p-decylcarboxyphenyl-p'-carboxybenzyl ether

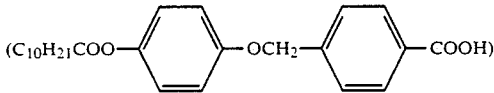

In 70 ml of a mixed solvent of methylene chloride and THF were dissolved 5 g of p-bromomethylbenzoic acid, 10 g of dihydropyran and 585 mg of pyridinium p-toluenesulfonate, and reaction was carried out at room temperature for 6 hours. The reaction mixture was washed with a saturated aqueous sodium hydrogencarbonate solution and saturated aqueous sodium chloride solution, and was concentrated and recrystallized from an n-hexane/ethyl acetate/chloroform mixed solvent to obtain 4.0 g of tetrahydropyranyl p-bromomethylbenzoate. Then, 267 mg of sodium hydride washed with n-pentane was dissolved in 10 ml of DMF, and a solution of 2 g of tetrahydropyranyl p-bromomethylbenzoate and 1.86 g of p-hydroxyphenyl decylcarboxylate in 10 ml of DMF was dropped into the above solution in a nitrogen atmosphere. The mixture was stirred overnight, and the reaction liquid was put in an ice cooled 1N aqueous hydrochloric acid solution and extracted with chloroform. The extract was concentrated, the concentrate was diluted with ethanol, 170 mg of pyridinium p-toluenesulfonate was added to the dilution, and the mixture was stirred at 55° C. for 1 hour. The mixture was diluted with chloroform and the dilution was washed with a saturated aqueous sodium chloride solution concentrated and recrystallized from a mixed solvent of acetate and chloroform to obtain 1.2 g of p-decylcarboxyphenyl-p'-carboxybenzyl ether.

REFERENTIAL EXAMPLE 9

Synthesis of p-dodecyloxycarbonyl-p'-carboxybenzil ether

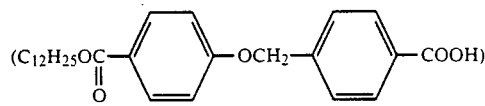

In 5 ml of DMF was dissolved 132 mg of sodium hydride washed with n-pentane, and a solution of 1.02 g of p- hydroxybenzoic acid and 2 g of tetrapyranyl p-bromomethylbenzoate synthesized according to the process described in Referential Example 8 in 10 ml of DMF was dropped into the above solution, and a reaction was carried out at room temperature overnight. The reaction liquid was put into a 1N aqueous solution of hydrochloric acid and the mixture was treated in the same manner as described in Referential Example 8. Recrystallization from a mixed solvent of ethyl acetate and chloroform gave 800 mg of p-dodecyloxycarbonylphenyl-p'-carboxybenzil ether.

REFERENTIAL EXAMPLE 10

Synthesis of 4-(4'-decyloxybenzoyloxy)benzoic acid

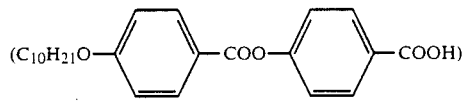

In 10 ml of pyridine was dissolved 2.3 g of benzyl p-hydroxybenzoate, a solution of 3 g of p-decyloxybenzoic acid chloride in 15 ml of pyridine was added to the above solution, and a reaction was carried out at room temperature overnight. The reaction liquid was put in ice-cooled dilute hydrochloric acid and the formed precipitate was recovered by filtration, dried and purified by the silica gel chromatography to obtain 4 g of benzyl 4-(4'-decyloxybenzoyloxy)benzoate. This ester was dissolved in 20 ml of ethyl acetate and 0.4 g of Pd/C was added. Catalytic reduction was carried out under a hydrogen pressure of 2 kg/cm² overnight. The catalyst was removed by filtration, and ethyl acetate was evaporated from the reaction liquid to obtain 3.2 g of 4-(4'-decyloxybenzoyloxy)benzoic acid.

REFERENTIAL EXAMPLE 11

Synthesis of mono(4-decyloxyphenyl) terephthalate

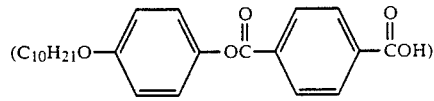

In 10 ml of dry benzene was dissolved 1.71 g of terephthaloyl dichloride, and 2.5 g of benzyl alcohol, 5 ml of triethylamine were added to the solution, and a reaction was carried out at room temperature with stirring overnight. The reaction liquid was poured into ice-cooled dilute hydrochloric acid, and ethyl acetate was added to the mixture, and an extraction was effected. The extract was washed with water and dried on MgSO4, the ethyl acetate was evaporated, and the residue was recrystallized from ethanol to obtain 3.2 g of benzyl terephthalate. Then, 1.7 g of this ester was dissolved in 20 ml of acetone and an equimolar amount of sodium hydroxide dissolved in a 1/1 mixed solvent of ethanol and water was added to the above solution, and the mixture was stirred overnight. Acetone was evaporated and the residue was extracted with dilute hydrochloric acid and ethyl acetate. The extract was washed with water and dried on MgSO4. Ethyl acetate was evaporated and the residue was recrystallized from a mixed solvent of acetone and water to obtain 1.0 g of monobenzyl terephthalate. Thionyl chloride was added to this ester to form an acid chloride, and unreacted thionyl chloride was removed by distillation under a reduced pressure. Then, 10 ml of pyridine and 1.2 g of decyloxyphenol were added to the acid chloride, and benzyl-4-decyloxyphenyl terephthalate was prepared in the same manner as described in Referential Example 10. Catalytic reduction was carried out by using Pd/C to obtain 1.6 g of mono(4-decyloxyphenyl) terephthalate.

REFERENTIAL EXAMPLE 12

Synthesis of 2-(4-hydroxyphenyl)-5-octyloxypyridine

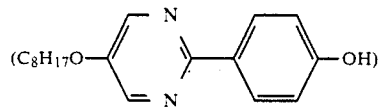

The intended compound was synthesized from 4-hydroxybenzamidine hydrochloride and β-dimethylamino-α-octyloxyacrolein by customary procedures by using sodium methoxide.

REFERENTIAL EXAMPLE 13

Synthesis of 3-chloro-4-dodecyloxyphenyl 4-hydroxybenzoate

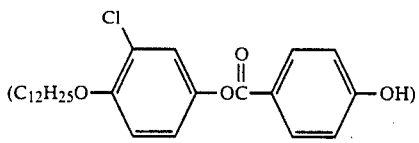

In ethanol, chlorohydroquinone was reacted with dodecylbromide in ethanol by using 1 equivalent of potassium hydroxide to obtain 3-chloro-4-dodecyloxyphenol. Then, 3.1 g of this 3-chloro-4-dodecyloxyphenol was reacted with 2.0 g of 2,4-acetoxybenzoic acid chloride in pyridine and the reaction mixture was treated by customary procedures to obtain 4 g of 3-chloro-4-dodecyloxyphenyl 4-acetoxybenzoate. This ester was dissolved in a THF/methanol liquid mixture and 1 equivalent of 1N LiOH was added to selectively isolate the acetoxy group, whereby 3-chloro-4-dodecyloxyphenyl 4-hydroxybenzoate was obtained.

REFERENTIAL EXAMPLE 14

Synthesis of 4'-dodecyloxycarbonylphenyl 3-chloro-4-hydroxybenzoate

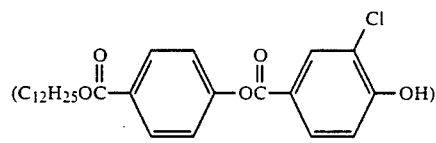

In 10 ml of pyridine was dissolved 2.0 g of 4-acetoxybenzoic acid chloride, and 2.4 g of dodecyl alcohol was added to the solution. Reaction was carried out at room temperature with stirring. The reaction mixture was treated by customary procedures to obtain 2.4 g of dodecyl 4-acetoxybenzoate. In the same manner as described in Referential Example 13, the acetoxy group was selectively isolated to quantitatively obtain dodecyl 4-hydroxybenzoate. This ester was dissolved in 20 ml of pyridine and a solution of 2.2 g of 3-chloro-4-benzyloxybenzoic acid chloride in 20 ml of pyridine was added to the above solution. The mixture was reacted at room temperature with stirring overnight and the reaction mixture was treated by customary procedures to obtain 3.3 g of 4'-dodecyloxycarbonylphenyl 3-chloro-4-benzyloxybenzoate. In the same manner as described in Referential Example 10, this ester was catalytically reduced to obtain 2.7 g of 4'-dodecyloxycarbonylphenyl 3-chloro-4-hydroxybenzoate.

REFERENTIAL EXAMPLE 15

Synthesis of 4'-hydroxyphenyl 4-dodecyloxybenzoate

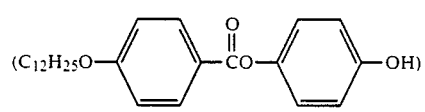

In 30 ml of pyridine, 3.25 g of 4-dodecyloxybenzoic acid chloride was reacted with 2.0 g of hydroquinone monobenzyl ether to obtain 4.4 g of 4'-benzyloxyphenyl 4-dodecyloxybenzoate. This ester was catalytically reduced in the same manner as described in Referential Example 10 to obtain 3.6 g of 4'-hydroxyphenyl 4-dodecyloxybenzoate.

REFERENTIAL EXAMPLE 16

Synthesis of 4-(4'heptyloxybenzyloxy)benzoic acid

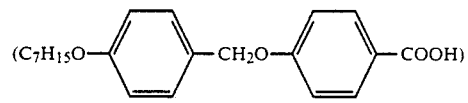

In 20 ml of benzene were dissolved 2.2 g of 4-heptyloxybenzyl alcohol and 1.7 g of ethyl 4-hydroxybenzoate, 1.8 g of diethyl azodicarboxylate and 2.6 g of triphenylphosphine were added to the solution, and a reaction was carried out with stirring. The reaction liquid was concentrated and the concentrate was separated and purified by the silica gel chromatography to obtain 3.1 g of ethyl 4-(4'-heptyloxybenzyloxy)benzoate. This ester was dissolved in 20 ml of ethanol and 4.2 ml of a 2N aqueous KOH solution was added to the solution to effect the hydrolysis. The reaction mixture was treated by customary procedures to obtain 2.7 g of 4-(4'heptyloxybenzyloxy)benzoic acid.

REFERENTIAL EXAMPLE 17

Synthesis of 4'-decyloxy-3-fluoro-4-hydroxybiphenyl

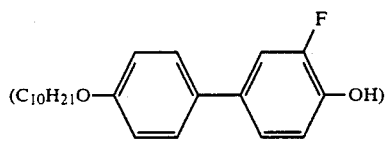

In 30 ml of methylene chloride was dissolved 3.3 g of 4'-decyloxy-4-hydroxybiphenyl, 3.2 g of N-fluoro-3,5-dichloropyridinium trifluorate was added to the solution, and a reduction reaction was carried out for 5 hours in an argon atmosphere. Then, 0.2 g of potassium iodide was added to the reaction mixture to deactivate unreacted N-fluoro-3,5-dichloropyridinium trifluorate, 80 ml of ethyl ether was added, and insoluble substances were removed by filtration. The filtrate was concentrated and the concentrate was separated and purified by the silica gel chromatography to obtain 2.0 g of 4'-decyloxy-3-fluoro-2-hydroxybiphenyl.

REFERENTIAL EXAMPLE 18

Synthesis of 2-(4'-hydroxyphenyl)-5-hexylpyrimidine

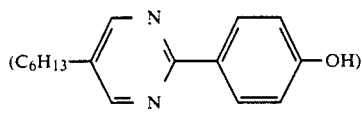

By customary procedures, 4-benzyloxyphenylamidine hydrochloride was coupled with diethyl 2-hexylmalonate by using sodium methoxide as the catalyst, a chlorine substitution was carried out with phosphorus oxychloride, and a catalytic reduction was carried out with Pd/C to obtain the intended compound.

REFERENTIAL EXAMPLE 19

Synthesis of hydroquinone mono-(4-octyloxycarbonyl)benzyl ether

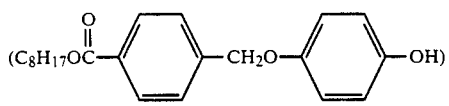

In 30 ml of benzene was dissolved 2.3 g of 4-bromomethylbenzoic acid chloride, 1.37 g of n-octyl alcohol and 5 ml of triethylamine were added to the solution, and a reaction was carried out at room temperature with stirring overnight. Then, 30 ml of ethyl acetate and 10 ml of 2N HCl were added to the reaction mixture, and the organic layer was separated, washed with water and dried on magnesium sulfate. The solvent was removed by distillation, and the residue was separated and purified by the silica gel column chromatography to obtain 3.0 g of octyl 4-bromomethylbenzoate.

Separately, 0.4 g of 60% oily sodium hydride was washed with n-pentane, dried and suspended in DMF, a solution of 1.52 g of hydroquinone monoacetate in 15 ml of DMF was dropped in the suspension, and the mixture was stirred for 2 hours. Then, a solution of 3.3 g of octyl 4-bromomethylbenzoate in DMF was dropped into the mixture and a reaction was carried out at room temperature with stirring overnight. The reaction liquid was poured into water, and insoluble substances were separated by filtration, dissolved in chloroform, washed with dilute hydrochloric acid and water, and dried on MgSO₄. The solvent was removed by distillation and the residue was dissolved in a mixed solvent of THF and methanol, and 2 ml of 1N LiOH was added to the solution and deacetylation was carried out by customary procedures to obtain 2.1 g of hydroquinone mono-(4-ocyloxycarbonyl)benzyl ether.

REFERENTIAL EXAMPLE 20

Synthesis of 4-(4'-undecylcarboxybenzoyloxy)benzoic acid

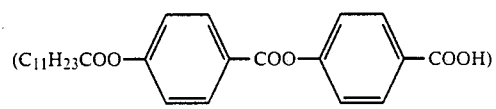

By customary procedures, 3.5 g of benzyl 4-undecylcarboxybenzoate was prepared from 2.3 g of benzyl 4-hydroxybenzoate and 2.5 g of lauric acid chloride, and this ester was catalytically reduced under a hydrogen pressure of 2 kg/cm² by using Pd/C as the catalyst to obtain 2.8 g of 4-undecylcarboxybenzoic acid. The acid was converted to 4-undecylcarboxybenzoic acid chloride by thionyl chloride and the acid chloride was reacted with 1.8 g of benzyl 4-hydroxybenzoate to form benzyl 4-(4-undecylcarboxybenzoyloxy)benzoate. The ester was catalytically reduced under a hydrogen pressure of 2 kg/cm² by using Pd/C as the catalyst to isolate the benzyl group and obtain 3.0 g of 4-(4'undecylcarboxybenzoyloxy)benzoic acid.

REFERENTIAL EXAMPLE 21

Synthesis of 4'-undecylcarboxybiphenylcarboxylic acid

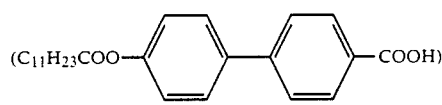

In 20 ml of benzene was suspended 2.14 g of 4'-hydroxybiphenylcarboxylic acid, 2.5 g of lauric acid chloride and 5 ml of triethylamine were added to the suspension, and a reaction was carried out under reflux at 80° C. for 4 hours. Chloroform was added to the reaction mixture and the mixture was washed with dilute hydrochloric acid and distilled water. The organic layer was then separated, dried on magnesium sulfate, concentrated and purified by the silica gel column chromatograpy to obtain 3.0 g of 4'-undecylcarboxybiphenylcarboxylic acid.

EXAMPLE 1

In 50 ml of tetrahydrofuran were dissolved 150 mg of (2S,5R)-2-hydroxy-5-hexyl-δ-valerolactone synthesized by the process described in Referential Example 4, 762 mg of p-decyloxybiphenylcarboxylic acid synthesized by the process described in Referential Example 5, and 295 mg of triphenylphosphine, 170 μl of diethyl azodicarboxylate was added to the solution, and a reaction was carried out with stirring overnight. The reaction mixture was concentrated and the concentrate was separated and purified in a silica gel column by using n-hexane/ethyl acetate/chloroform as the developing solvent. Recrystallization from ethyl acetate gave 50 mg of (2R5S)-2-[(4'-decyloxybiphenyl)-4-carbonyloxy]-5hexyl-δ-valerolactone.

The NMR spectrum of this compound is shown in FIG. 1.

When the phase transition behavior of this compound was examined by heating to melt the compound under observation with a polarization microscope, the compound showed the following phase transition:

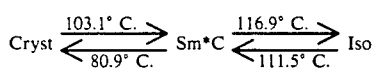

Note, Cryst. indicates the crystalline phase, Sm*C indicates the chiral smectic phase, Iso indicates the isotropic phase, smX indicates an unidentified smectic phase, the arrow indicates the transition to the shown phase, and the temperature described in the vicinity of the arrow indicates the temperature of the transition to the shown phase.

EXAMPLE 2

In 20 ml of benzene were dissolved 67 mg of (2S,5R)-2-hydroxy-5-hexyl-δ-valerolactone synthesized by the process described in Referential Example 4, 420 mg of p-decylcarboxyphenyl-p'-carboxybenzyl ether synthesized by the process described in Referential Example 8 and 400 mg of triphenylphosphine, 200 µl of diethyl azodicarboxylate was dropped into the solution, and a reaction was carried out with stirring overnight. The reaction liquid was concentrated, and the concentrate was separated and purified by the silica gel column chromatography. Recrystallization from ethyl acetate gave 70 mg of the intended compound. From the NMR spectrum, it was confirmed that the obtained compound was the intended compound represented by the following formula:

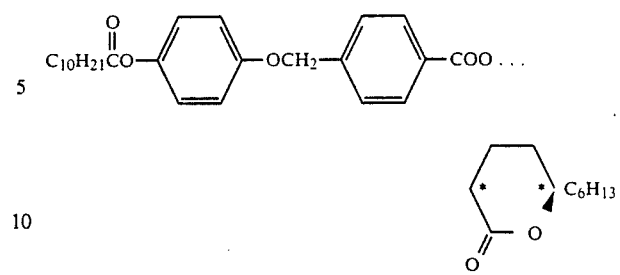

Figure 2:
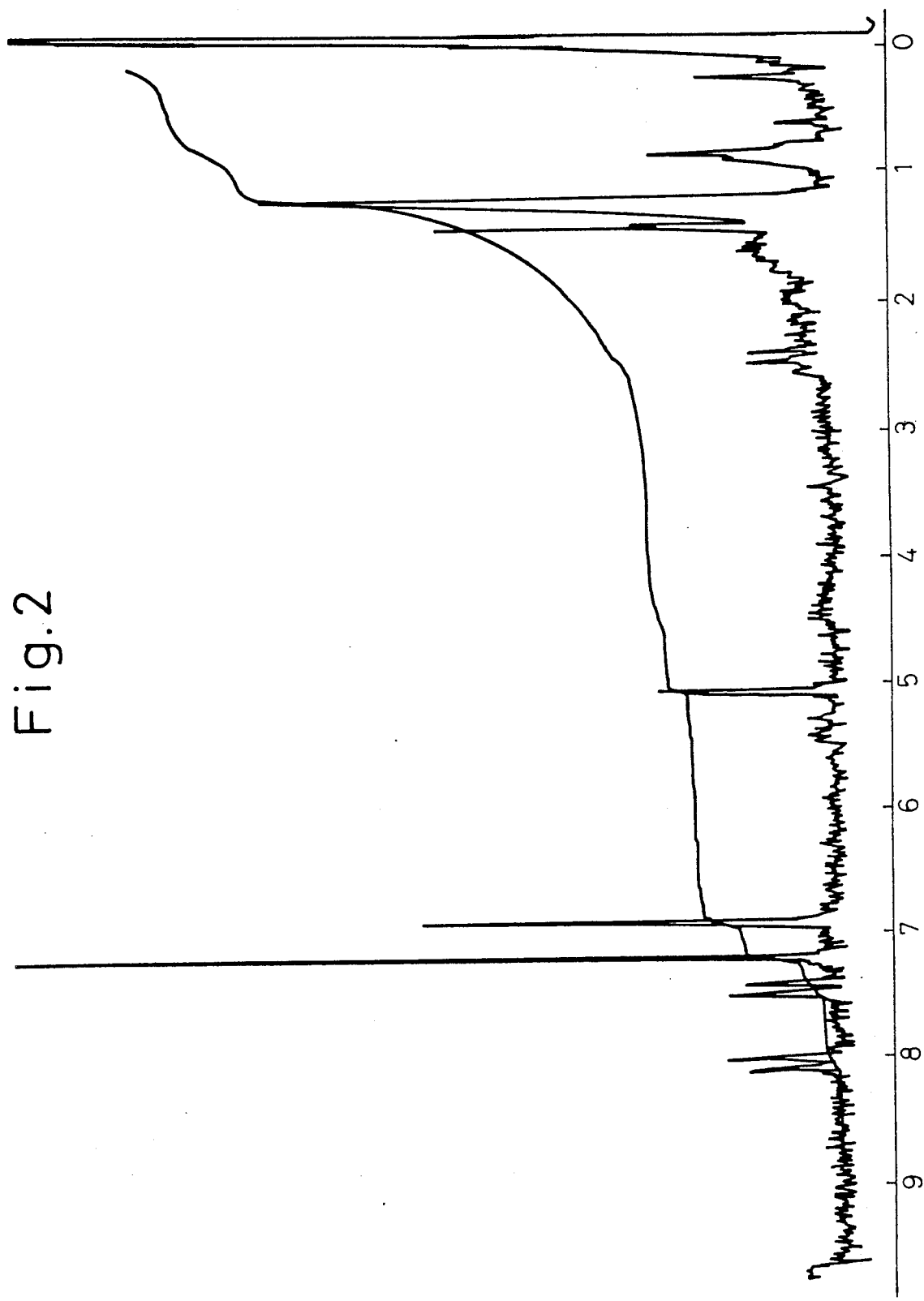

The NMR spectrum of the compound is shown in FIG. 2.

The phase transition behavior of this compound was determined by using a differential scanning calorimeter and a polarization microscope. The results are shown below:

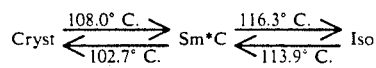

Figure 3:
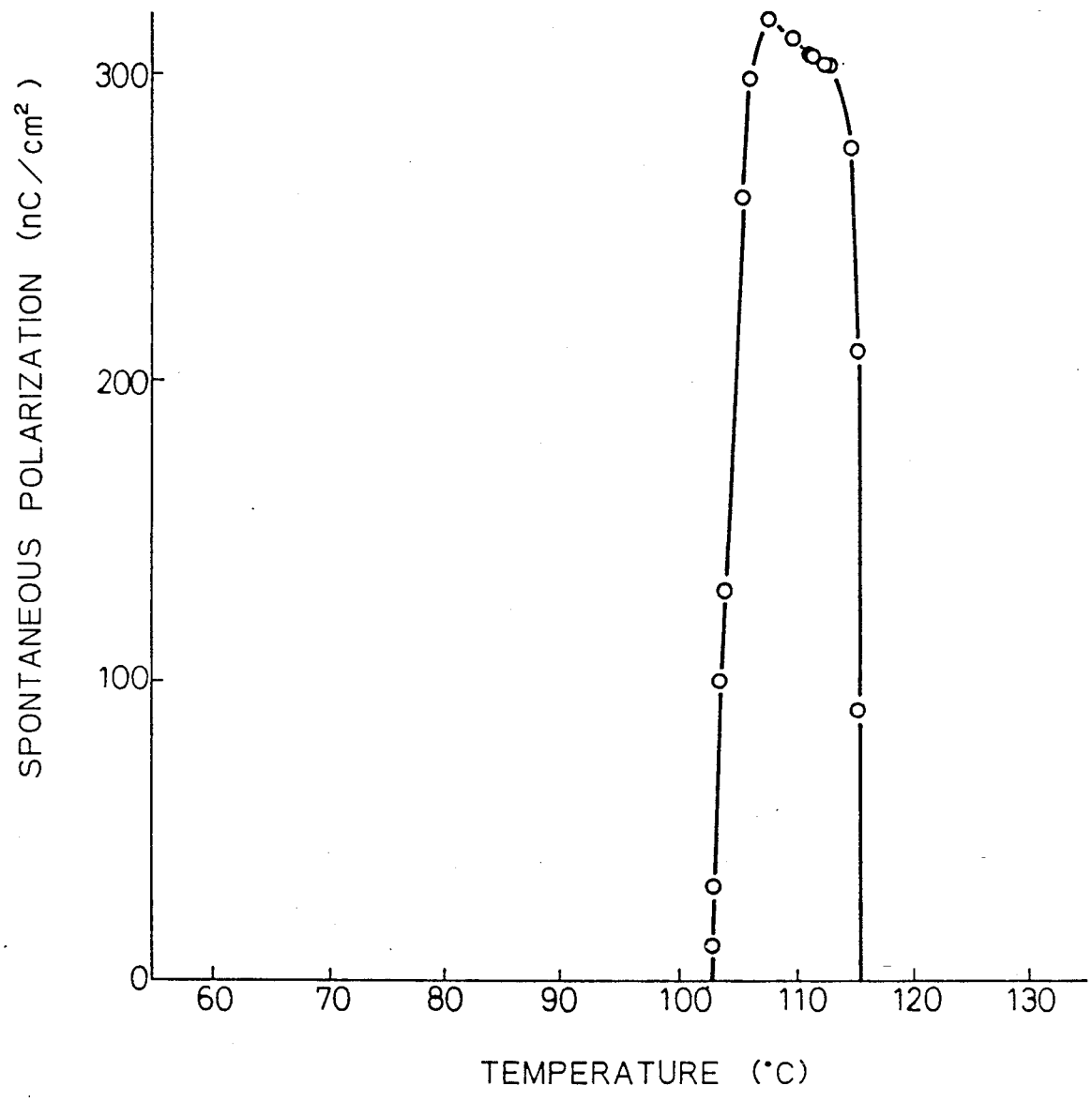
FIGS. 3, 4, 5 and 6 show the temperature dependency of the spontaneous polarization.

The temperature dependency of the spontaneous polarization of this compound, measured under the conditions of a cell thickness of 50 µm, a frequency of 100 Hz, and a peak voltage of ±100 V, by the triangular wave method, is shown in FIG. 3.

EXAMPLES 3 THROUGH 19

The compounds shown in Table 1 were synthesized in the same manner as described in Example 2 except that a predetermined amount of a compound shown in Table 1 was used instead of 420 mg of p-decylcarboxyphenyl-p'-carboxybenzyl ether and the valerolactone derivative was used in an amount shown in Table 1, and the phase transition temperatures of these compounds were examined. The results are shown in Table 1.

Figure 6:
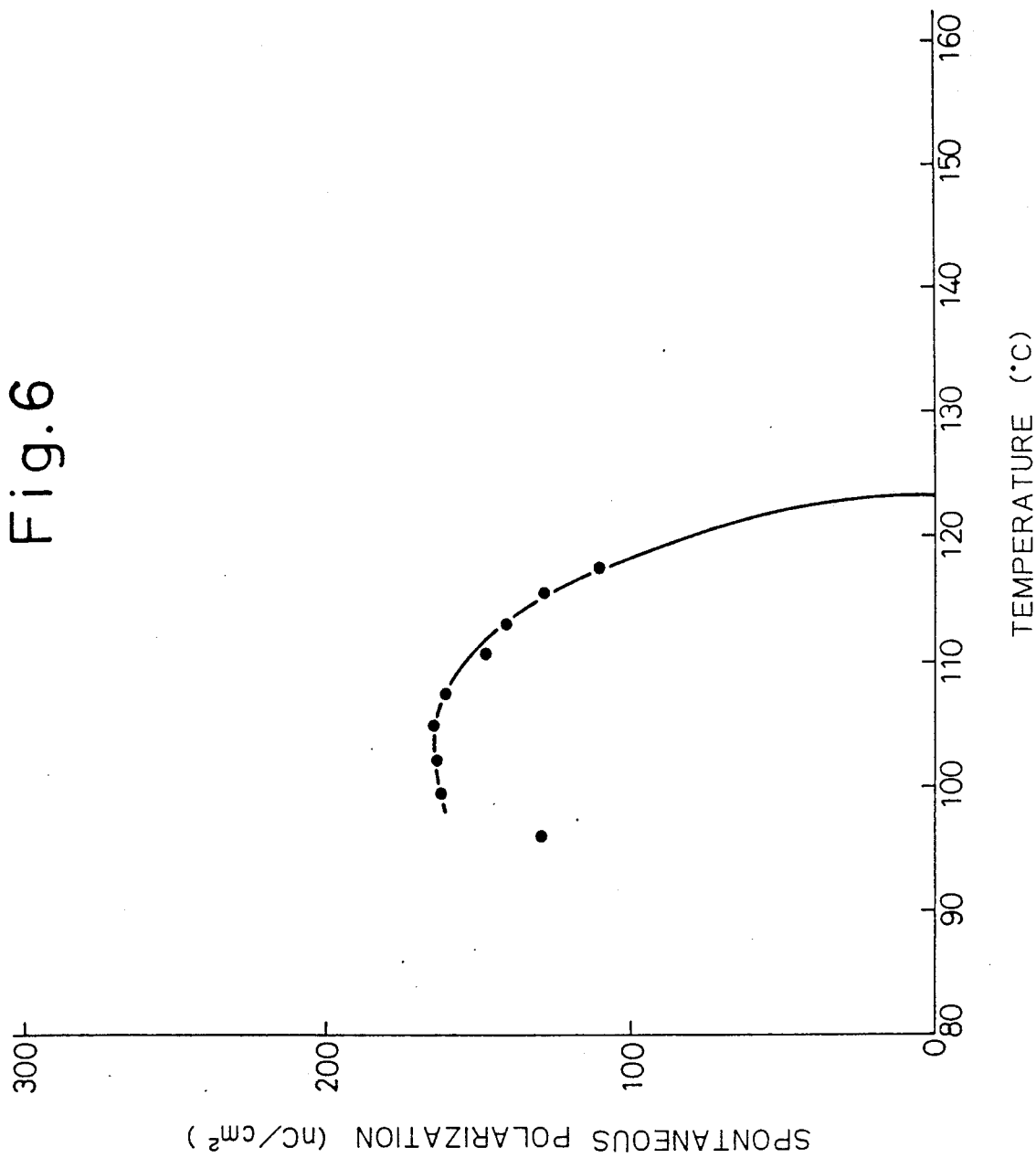

The temperature dependency of the spontaneous polarization of the compound obtained in Example 16 is shown in FIG. 6.

TABLE 1

| Example No. | Charged composition | | Obtained compound and amount thereof | Phase transition temperature |
|---|---|---|---|---|
| | (2S, 5R)-2-hydroxy-5-hexyl-δ-valerolactone | Compound of Referential Example | | |
| 3 | 180 mg | $C_{12}H_{25}OC(=O)$-C$_6$H$_4$-OCH$_2$-C$_6$H$_4$-COOH, $C_{12}H_{25}O$-C$_6$H$_4$-OCH$_2$-C$_6$H$_4$- (Ref. Ex. 9) 630 mg | $C_{12}H_{25}OC(=O)$-C$_6$H$_4$-OCH$_2$-C$_6$H$_4$-CO-O-[lactone with C$_6$H$_{13}$] 150 mg | Cryst. $\xrightarrow{99.6°C}$ Iso; Iso $\xrightarrow{95.5°C}$ Sm*C; Sm*C $\xrightarrow{95°C}$ Cryst. |
| 4 | 190 mg | $C_{12}H_{25}O$-C$_6$H$_4$-OCH$_2$-C$_6$H$_4$-COOH (Ref. Ex. 7) 450 mg | $C_{12}H_{25}O$-C$_6$H$_4$-OCH$_2$-C$_6$H$_4$-CO-O-[lactone with C$_6$H$_{13}$] 300 mg | Cryst. $\xrightarrow{107.2°C}$ Iso; Iso $\xrightarrow{102.0°C}$ Sm*C; Sm*C $\xrightarrow{101.6°C}$ Cryst. |
| 5 | 190 mg | $C_{13}H_{27}O$-C$_6$H$_4$-OCH$_2$-C$_6$H$_4$-COOH (Ref. Ex. 7) 500 mg | $C_{13}H_{27}O$-C$_6$H$_4$-OCH$_2$-C$_6$H$_4$-CO-O-[lactone with C$_6$H$_{13}$] 320 mg | Cryst. $\xrightarrow{110.3°C}$ Sm*C $\xrightarrow{116.6°C}$ Iso; Iso $\xrightarrow{114.7°C}$ Sm*C $\xrightarrow{104.0°C}$ Cryst. |

TABLE 1-continued

| Example No. | Charged composition | | Obtained compound and amount thereof | Phase transition temperature |
|---|---|---|---|---|
| | (2S, 5R)-2-hydroxy-5-hexyl-δ-valerolactone | Compound of Referential Example | | |
| 6 | 100 mg (structure: δ-valerolactone with OH and C₆H₁₃) | C₁₀H₂₁O–⟨phenyl⟩–OCO–⟨phenyl⟩–COOH (Ref. Ex. 10) 300 mg | C₁₀H₂₁O–⟨phenyl⟩–OCO–⟨phenyl⟩–CO–O–(lactone with C₆H₁₃) 150 mg | Cryst ⇌(106.4°C / 99.5°C) Sm*C ⇌ 111°C Iso |
| 7 | 100 mg | C₁₀H₂₁O–⟨phenyl⟩–OC–⟨phenyl⟩–COOH (Ref. Ex. 11) 300 mg | C₁₀H₂₁O–⟨phenyl⟩–OC–⟨phenyl⟩–CO–O–(lactone with C₆H₁₃) 170 mg | Cryst ⇌(109.1°C / 99.1°C) Sm*C ⇌ 122.4°C Ch ⇌ 126°C Iso |
| 8 | 100 mg | C₈H₁₇O–⟨pyrimidine⟩–⟨phenyl⟩–OH (Ref. Ex. 12) 200 mg | C₈H₁₇O–⟨pyrimidine⟩–⟨phenyl⟩–O–(lactone with C₆H₁₃) 120 mg | Cryst ⇌(100.9°C / 89.9°C) Iso |

TABLE 1-continued

| Example No. | Charged composition | | Obtained compound and amount thereof | Phase transition temperature |
|---|---|---|---|---|
| | (2S, 5R)-2-hydroxy-5-hexyl-δ-valerolactone | Compound of Referential Example | | |
| 9 | [lactone structure with OH, C₆H₁₃] 100 mg | [aromatic diester with Cl, C₁₂H₂₅O] (Ref. Ex. 13) 300 mg | [product structure with Cl, C₁₂H₂₅O, C₆H₁₃] 140 mg | Cryst $\xrightarrow{79.5°C.}_{66.7°C.}$ SmX $\xrightarrow{93.6°C.}_{}$ Iso |
| 10 | [lactone structure with OH, C₆H₁₃] 100 mg | [aromatic diester with Cl, C₁₂H₂₅O] (Ref. Ex. 14) 300 mg | [product structure with Cl, C₁₂H₂₅O, C₆H₁₃] 150 mg | Cryst $\xrightarrow{66°C.}_{36°C.}$ Iso |
| 11 | [lactone structure with OH, C₆H₁₃] 100 mg | [aromatic diester with C₁₂H₂₅O] (Ref. Ex. 15) 300 mg | [product structure with C₁₂H₂₅O, C₆H₁₃] 130 mg | Cryst $\xrightarrow{83°C.}_{72°C.}$ Iso |

TABLE 1-continued

| Example No. | Charged composition | Compound of Referential Example | Obtained compound and amount thereof | Phase transition temperature |
|---|---|---|---|---|
| | (2S, 5R)-2-hydroxy-5-hexyl-δ-valerolactone | | | |
| 12 | [lactone structure with OH and C$_6$H$_{13}$] 100 mg | C$_7$H$_{15}$O–[phenyl]–CH$_2$O–[phenyl]–COOH (Ref. Ex. 16) 200 mg | C$_7$H$_{15}$O–[phenyl]–CH$_2$O–[phenyl]–CO–O–[lactone with C$_6$H$_{13}$] 160 mg | Cryst $\xrightleftharpoons[84.9°C.]{106.9°C.}$ Iso |
| 13 | [lactone structure with OH and C$_6$H$_{13}$] 100 mg | C$_{10}$H$_{21}$O–[phenyl]–[F-phenyl]–OH (Ref. Ex. 17) 200 mg | C$_{10}$H$_{21}$O–[phenyl]–[F-phenyl]–O–[lactone with C$_6$H$_{13}$] 170 mg | Cryst $\xrightleftharpoons[66.6°C.]{81.3°C.}$ Iso |
| 14 | [lactone structure with OH and C$_6$H$_{13}$] 100 mg | C$_6$H$_{13}$–[pyrazine]–[phenyl]–OH (Ref. Ex. 18) 200 mg | C$_6$H$_{13}$–[pyrazine]–[phenyl]–O–[lactone with C$_6$H$_{13}$] 200 mg | Cryst $\xrightleftharpoons[51.6°C.]{72.2°C.}$ Iso |

TABLE 1-continued

| Example No. | Charged composition | | Obtained compound and amount thereof | Phase transition temperature |
|---|---|---|---|---|
| | (2S, 5R)-2-hydroxy-5-hexyl-δ-valerolactone | Compound of Referential Example | | |
| 15 | 100 mg | C₈H₁₇OC-C₆H₄-CH₂O-C₆H₄-OH (Ref. Ex. 19) 200 mg | C₈H₁₇OC-C₆H₄-CH₂O-C₆H₄-O-[lactone with C₆H₁₃] 150 mg | Cryst →54.8°C Iso; Iso →52.5°C SmX; →35.1°C Cryst |
| 16 | 100 mg | C₇H₁₅O-biphenyl-COOH (Ref. Ex. 5) 200 mg | C₇H₁₅O-biphenyl-CO-O-[lactone with C₆H₁₃] 160 mg | Cryst →117.8°C Sm*C →123.3°C Iso; →98.2°C |
| 17 | 100 mg | C₁₆H₃₃O-biphenyl-COOH (Ref. Ex. 5) 200 mg | C₁₆H₃₃-biphenyl-CO-O-[lactone with C₆H₁₃] 180 mg | Cryst →110.5°C Sm*C →127.4°C Iso; →98.1°C |

TABLE 1-continued

| Example No. | Charged composition | | Obtained compound and amount thereof | Phase transition temperature |
|---|---|---|---|---|
| | (2S, 5R)-2-hydroxy-5-hexyl-δ-valerolactone | Compound of Referential Example | | |
| 18 | [structure with F, OH, C₆H₁₃, lactone] 100 mg | [biphenyl dicarboxylic acid structure with C₁₁H₂₃CO] (Ref. Ex. 20) 300 mg | [biphenyl diester with C₁₁H₂₃CO and lactone with C₆H₁₃] 150 mg | Cryst $\xrightarrow{130.6° C.}$ Iso / $\xleftarrow{125.2° C.}$ Sm*C / $\xleftarrow{123.7° C.}$ |
| 19 | [structure with F, OH, C₆H₁₃, lactone] 100 mg | [biphenyl carboxylic acid structure with C₁₁H₂₃CO] (Ref. Ex. 21) | [biphenyl ester with C₁₁H₂₃CO and lactone with C₆H₁₃] | Cryst $\xrightleftharpoons[109.1° C.]{126.5° C.}$ Sm*C $\xrightarrow{140.1° C.}$ Iso |

EXAMPLE 20

By customary procedures, 3-chloro-4-hydroxybenzoic acid was reacted with dodecylbromide in a mixed solution of ethanol and water containing sodium hydroxide to produce 3-chloro-4-dodecyloxybenzoic acid, and this acid was reacted with thionyl chloride to obtain 3-chloro-4-dodecyloxybenzoic acid chloride. Separately, 100 mg of (2S,5R)-2-hydroxy-5-hexyl-δ-valerolactone and 200 mg of 4-benzyloxybenzoic acid were dissolved in 200 ml of benzene, 190 mg of diethyl azodicarboxylate and 250 mg of triphenylphosphine were added to the solution, and a reaction was carried out at room temperature with stirring overnight. The reaction mixture was concentrated under a reduced pressure, and the concentrate was separated and purified by the silica gel column chromatography to obtain 120 mg of 2-(4'-benzyloxybenzoyloxy)-5-hexyl-δ-valerolactone. This compound was catalytically reduced under a hydrogen pressure of 2 kg/cm² by using Pd/C as the catalyst to obtain 2-(4'-hydroxy-benzoyloxy)-5-hexyl-δ-valerolactone. The obtained compound was dissolved in 20 ml of benzene, and 200 mg of 3-chloro-4-dodecyloxybenzoic acid chloride described above, 200 mg of triethylamine and 20 mg of N,N-dimethylaminopyridine were added to the solution, and a reaction was carried out with stirring overnight. The reaction liquid was treated by customary procedures and the intended product was separated and purified by the silica gel column chromatography. Recrystallization from ethanol gave 80 mg of (2R,5S)-2-[4-(3'-chloro-4'-dodecyloxybenzoyloxy)-benzoyloxy]-5-hexyl-δ-valeerolactone

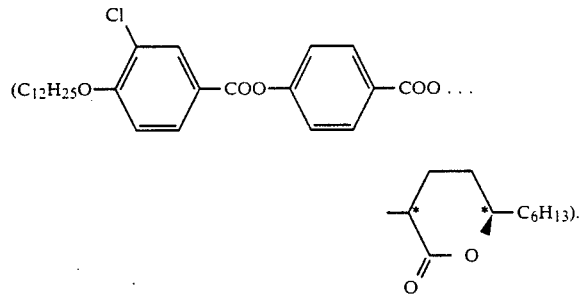

From the NMR spectrum and infrared absorption spectrum, it was confirmed that the intended compound was obtained. The phase transition temperature of the compound was as shown below:

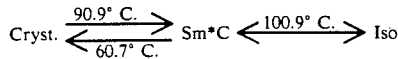

EXAMPLE 21

To a solution of 2.6 g of 4-hydroxy-4'-decyloxybiphenyl synthesized by the process described in Referential Example 6 in 50 ml of anhydrous pyridine was added 5 g of 4-acetoxybenzoic acid chloride, and the mixture was stirred at room temperature for 4 hours. The reaction liquid was put in ice water and extracted with chloroform. The extract was washed with a saturated aqueous copper sulfate solution, a saturated aqueous sodium hydrogencarbonate solution and a saturated aqueous sodium chloride solution in sequence, dried on magnesium sulfate and concentrated. The concentrate was recrystallized from chloroform to obtain 1.7 g of 4'-(4''-decyloxy)biphenyl-4-acetoxybenzoate. Then, 1.0 g of this 4'(4''-decyloxy)biphenyl-4-acetoxybenzoate was dissolved in 100 ml of tetrahydrofuran, and 10 ml of methanol, 4 ml of water and 2 ml of a 1N aqueous solution of lithium hydroxide were added to the solution and the mixture was stirred at room temperature for 2 hours. Then, a saturated aqueous sodium hydrogencarbonate solution was added to the mixture and the mixture was extracted with chloroform. The extract was dried on magnesium sulfate and concentrated, and the concentrate was recrystallized from chloroform to obtain 0.6 g of 4'-(4''-decyloxy)biphenyl-4-hydroxybenzoate. Then, 0.6 g of this 4'-(4''-decyloxy)biphenyl-4-hydroxybenzoate, 180 mg of (2S,5R)-2-hydroxy-5-hexyl-δ-valerolactone synthesized by the process described in Referential Example 4 and 400 mg of triphenylphosphine were dissolved in 20 ml of tetrahydrofuran, 200 μl of diethyl azodicarboxylate was added to the solution, and the mixture was reacted at room temperature with stirring overnight. The reaction liquid was concentrated and the concentrate was separated and purified by the silica gel chromatography. Recrystallization from acetyl acetate gave 150 mg of the intended compound.

From the elementary analysis results, the NMR spectrum and the IR spectrum, it was confirmed that the obtained compound was a substance represented by the following chemical formula:

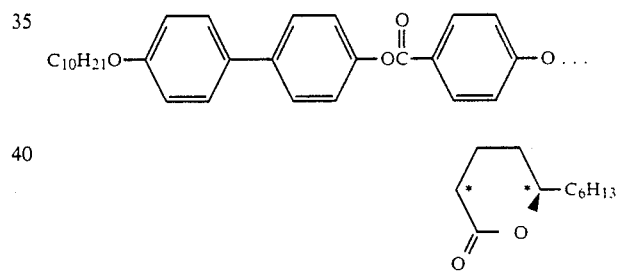

Analysis data of the compound are as follows.

| | Elementary Analysis Values | |
|---|---|---|
| | C(%) | H(%) |
| Found values | 76.17 | 8.34 |
| Calculated values | 76.40 | 8.33 |
| IR Vmax | 2950 – 2850 cm⁻¹ (S), 1720 cm⁻¹ (S), 1600 cm⁻¹ (S), 1495 cm⁻¹ (S), 1260 cm⁻¹ (S), 1205 cm⁻¹ (m), 1190 cm⁻¹ (m), 1165 cm⁻¹ (S), 1070 cm⁻¹ (S) | |
| ¹H-NMR δ (CDCl₃) | 0.8–1.0 (3 H, t) 1.1–2.4 (33 H, m) 3.9–4.05 (2 H, t) 4.3–4.6 (1 H, m) 4.7–4.9 (1 H, t) 6.8–8.2 (12 H, m) | |

The phase transition behavior of the compound, determined according to the method described in Example 2, was as shown below:

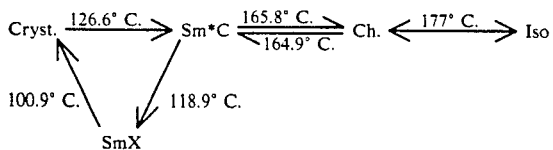

Figure 4:
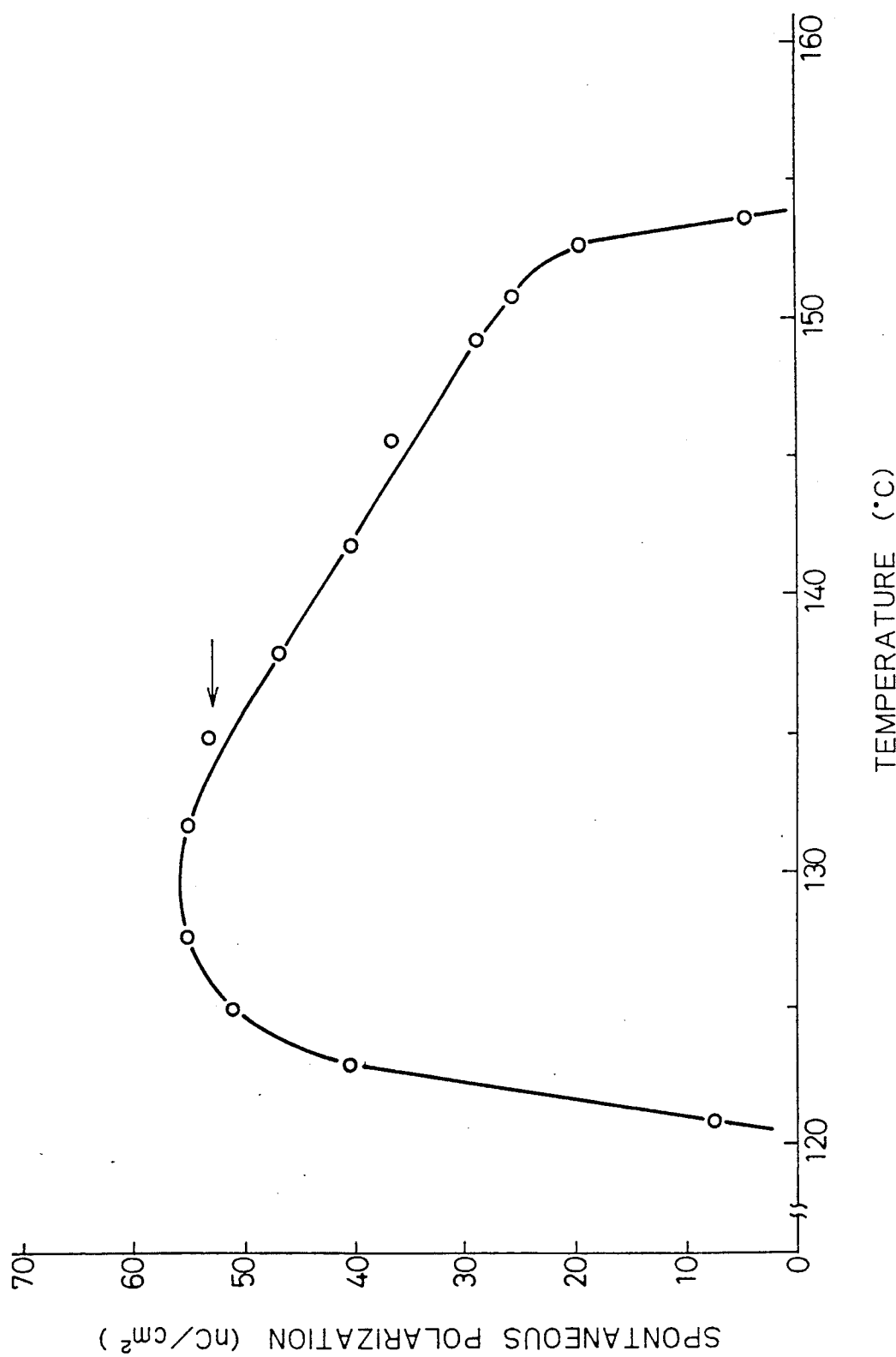

The temperature dependency of the spontaneous polarization of the compound, determined under the same conditions as described in Example 2, is shown in FIG. 4.

EXAMPLE 22

Figure 5:
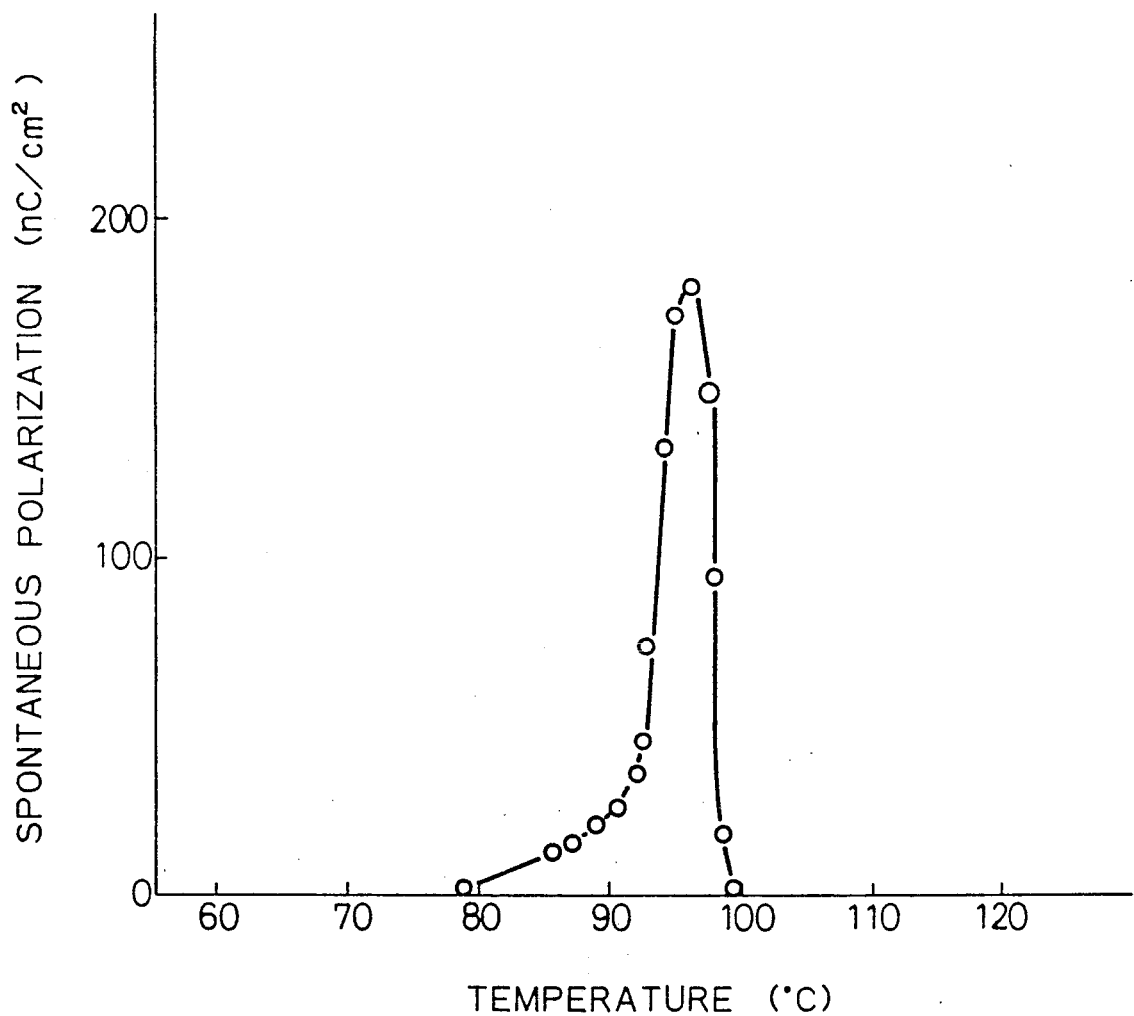

A liquid crystal composition was prepared by mixing and dissolving 50 mg of the compound synthesized in Example 3 and 50 mg of the compound synthesized in Example 4. The spontaneous polarization of the composition was determined in the same manner as described in Example 1. The results are shown in FIG. 5. Each of these compounds showed the ferroelectric phase (Sm*C phase) on a very narrow temperature range of 0.5° C. when used alone, but if these compounds were mixed, the ferroelectric phase-showing temperature range was expanded. It was also found that these compounds had a large spontaneous polarization.

EXAMPLE 23

In 50 ml of THF were dissolved 100 mg of (2S,5R)-2-hydroxy-5-hexyl-δ-valerolactone synthesized by the process described in Referential Example 4, 260 mg of 4-hydroxy-4'-decyloxybiphenyl and 200 mg of triphenylphosphine, 150 μl of diethyl azodicarboxylate was dropped into the solution, and a reaction was carried out at room temperature with stirring overnight. The reaction liquid was concentrated, and the concentrate was separated and purified by the silica gel chromatography. A recrystallization from ethyl acetate gave 40 mg of the intended compound. From the NMR spectrum, it was confirmed that the obtained compound was a substance represented by the following chemical formula:

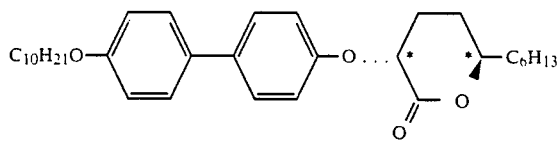

The compound had no liquid crystal characteristics, as shown below:

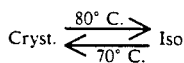

When 10 mg of this compound was dissolved in 90 mg of ferroelectric liquid crystal DOBAMBC [(S)-2-methylbutyl p-decyloxyphenylbenzylidene-aminocinnamate] and the spontaneous polarization was measured under the same conditions as described in Example 2, it was found that the maximum value was 15 nC/cm², and it was confirmed that the compound was effective as an additive to a ferroelectric liquid crystal.

EXAMPLE 24

A ferroelectric liquid crystal composition was prepared by incorporating 20 mole% of a compound of the present invention, shown in Table 2, into a liquid crystal composition having no ferroelectric characteristic and comprising the following alkoxypyrimidine analogues (A) through (F) [equimolar mixture of the alkoxypyrimidine analogues (A) through (F)]:

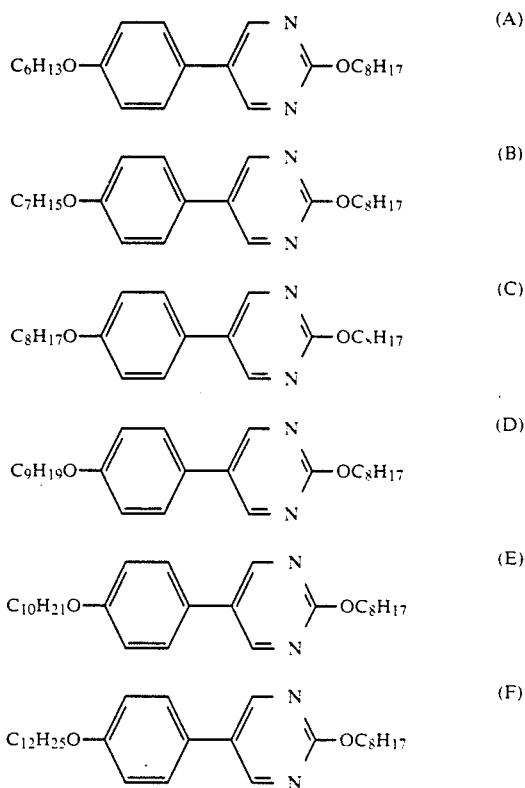

The phase transition temperature of the alkoxypyrimidine analogue composition was as shown below:

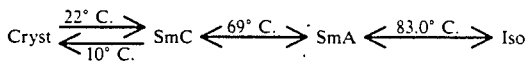

The phase transition temperature of the ferroelectric liquid crystal composition prepared according to the present invention was as shown in Table 2.

TABLE 2

| Chemical Formula of Compound of Present Invention | Phase Transition Temperature of Composition |
|---|---|
| ![compound] C₆H₁₃-pyrimidine-phenyl-O-*-*-C₆H₁₃ lactone | Cryst. ⇌(50°C/45°C) Sm*C →(60°C) Ch. →(72°C) Iso |

TABLE 2-continued

| Chemical Formula of Compound of Present Invention | Phase Transition Temperature of Composition |
|---|---|
| 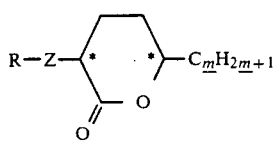 | Cryst $\xrightleftharpoons[42° C.]{50° C.}$ Sm*C $\xrightleftharpoons{77° C.}$ Iso |
| 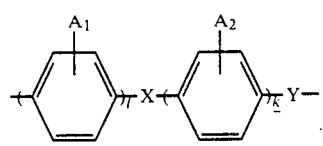 | Cryst $\xrightleftharpoons{25° C.}$ Sm*C $\xrightleftharpoons{77° C.}$ Ch. $\xrightleftharpoons{85° C.}$ Iso |

From the results shown in Table 2, it can be seen that a compound of the present invention, which has no ferroelectric characteristic when used alone, has a valuable effect in that, if the compound is mixed with another compound showing the smectic C phase, a ferroelectric characteristic is manifested.

As apparent from the foregoing description, the optically active compound of the present invention is chemically stable, as is clear from the chemical structure thereof, and the compound of the present invention is not discolored and has an excellent light stability. Accordingly, the compound of the present invention is valuable as a ferroelectric liquid crystal having a large spontaneous polarization or as a component to be added to a ferroelectric liquid crystal composition. Furthermore, the liquid crystal composition of the present invention shows a ferroelectric liquid crystal characteristic in a broad temperature range, including the practical temperature range, and has a large spontaneous polarization.

We claim:

1. An optically active compound having a δ-valerolactone ring, which is a ferroelectric liquid crystal represented by the following general formula (1):

$$R-Z-\overset{*}{\underset{}{\diagup}}\overset{*}{\underset{O}{\diagdown}}-C_mH_{2m+1} \quad (1)$$

wherein m is an integer of from 1 to 8, Z is a group represented by the following formula:

$$-\underset{A_1}{\diagup}\!\!\!\diagdown-X-\underset{A_2}{\diagup}\!\!\!\diagdown-Y-$$

in which each of l and k is a number of 1 or 2 and l and k satisfy the requirement of $2 \leq (l+k) \leq 3$, X stands for a direct bond, $-\underset{O}{\overset{O}{\|}}\!C\!O-$, $-O\overset{O}{\overset{\|}{C}}-$, $-CH_2O-$ or $-OCH_2-$, Y stands for $-\underset{O}{\overset{O}{\|}}\!C\!O-$ or $-O-$, and
$A_1$ and $A_2$ independently stand for $-H$, $-F$ or $-Cl$,

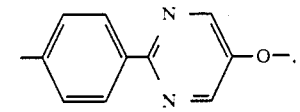

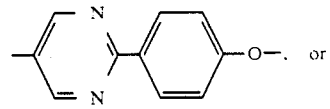

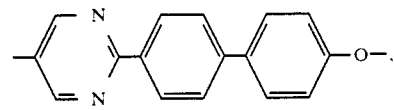

R stands for $-C_nH_{2n+1}$, $-OC_nH_{2n+1}$, $-OCC_nH_{2n-1}\overset{O}{\overset{\|}{}}$ or $-COC_nH_{2n-1}\overset{O}{\overset{\|}{}}$ in which n is an integer of from 1 to 18, and * indicates the asymmetric carbon atom.

2. A liquid crystal composition comprising an optically active compound having a δ-valerolactone ring, which is represented by the following general formula (1):

$$R-Z-\overset{*}{\underset{}{\diagup}}\overset{*}{\underset{O}{\diagdown}}-C_mH_{2m-1} \quad (1)$$

wherein Z, m, R and * are as defined in claim 1.

* * * * *

UNITED STATES PATENT AND TRADEMARK OFFICE
CERTIFICATE OF CORRECTION

PATENT NO. : 5,045,228

DATED : September 3, 1991

INVENTOR(S) : Jun Nakauchi, Mioko Uematsu, Keiichi Sakashita, Yoshitaka Kageyama and Kenji Mori It is certified that error appears in the above-identified patent and that said Letters Patent is hereby corrected as shown below:

On title page and col. 1, lines 1-3, change "XI-VALEROLACTONE" to --$\delta$-VALEROLACTONE--.

Claim 2, column 54, line 56 after "comprising" insert --a plurality of ferroelectric liquid crystal compounds, at least one of which is--.

Signed and Sealed this

Nineteenth Day of January, 1993

Attest:

DOUGLAS B. COMER

Attesting Officer    Acting Commissioner of Patents and Trademarks